US010634678B2

(12) United States Patent
Labus et al.

(10) Patent No.: US 10,634,678 B2
(45) Date of Patent: Apr. 28, 2020

(54) AMBRA-1 AND LORICRIN AS BIOMARKERS FOR DISEASE PROGRESSION IN MELANOMA

(71) Applicant: AMLO Biosciences Limited, Newcastle Upon Tyne (GB)

(72) Inventors: Marie Labus, Newcastle upon Tyne (GB); Penny Lovat, Newcastle upon Tyne (GB); Robert Ellis, Newcastle upon Tyne (GB)

(73) Assignee: AMLO Biosciences Limited, Newcastle Upon Tyne (GB)

( * ) Notice: Subject to any disclaimer, the term of this patent is extended or adjusted under 35 U.S.C. 154(b) by 110 days.

(21) Appl. No.: 15/525,655

(22) PCT Filed: Nov. 5, 2015

(86) PCT No.: PCT/GB2015/053347
§ 371 (c)(1),
(2) Date: May 10, 2017

(87) PCT Pub. No.: WO2016/075440
PCT Pub. Date: May 19, 2016

(65) Prior Publication Data
US 2018/0196050 A1 Jul. 12, 2018

(30) Foreign Application Priority Data
Nov. 10, 2014 (GB) .................... 1419976.4

(51) Int. Cl.
*G01N 33/574* (2006.01)
*G01N 33/577* (2006.01)

(52) U.S. Cl.
CPC ..... *G01N 33/5743* (2013.01); *G01N 2800/20* (2013.01); *G01N 2800/52* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| 2002/0151487 | A1* | 10/2002 | Nickoloff | A61K 38/177 514/19.6 |
| 2004/0213791 | A1* | 10/2004 | Bander | A61K 51/1072 424/155.1 |
| 2007/0059806 | A1* | 3/2007 | Arnon | C12N 15/115 435/91.1 |
| 2008/0113360 | A1* | 5/2008 | Riker | C12Q 1/6886 435/6.12 |
| 2010/0292331 | A1* | 11/2010 | Mitchell | G01N 33/57434 514/561 |
| 2012/0201750 | A1 | 8/2012 | Ryu | |

FOREIGN PATENT DOCUMENTS

| CN | 1909904 A | 2/2007 |
| CN | 103642927 | 3/2014 |
| JP | 2014128250 | 7/2014 |
| WO | WO-2009001392 | 12/2008 |
| WO | WO-2011133879 | 10/2011 |
| WO | WO-2013187983 | 12/2013 |
| WO | WO-2016075440 | 5/2016 |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Mantovani (European Journal of Cancer, vol. 30A, No. 3, p. 363-369, 1994) (Year: 1994).*
Rudikoff et al. (Proceedings of the National Academy of Sciences USA, vol. 79, p. 1979-1983, 1982) (Year: 1982).*
"International Application No. PCT/GB2015/053347, International Search Report and Written Opinion dated Jan. 26, 2016", (Jan. 26, 2016), 12 pgs.
Bhatia, Shailender, et al., "Treatment of Metastatic Melanoma: An Overview", Oncology (Williston Park). May 2009 ; 23(6): 488-496, (May 2009), 488-496.
Ellis, R. A., et al., "Abstract: Peritumoural expression of pro-autophagic Ambra-1 as a prognostic biomarker for melanoma", Skin Cancer Research, vol. 11, Supplement 7 (2013); Abstract #P205, (2013), 1 pg.
Lim, Andrea, et al., "Defining the Functional Role of the Autophagy Regulatory Gene Ambra-1 in Melanoma invasion and Metastasis", Poster presentation Newcastle University 2013; retrieved from the Internet: https://research.ncl.ac.uk/expeditionresearchscholarships/postergalleries/2013posters/Andrea%20Lim.pdf, (2013), 1 pg.
Riker, Adam I., et al., "The gene expression profiles of primary and metastatic melanoma yields a transition point of tumor progression and metastasis", BMC Medical Genomics 2008, 1:13, (Apr. 28, 2008), 16 pgs.
Verykiou, S., et al., "Peri-tumoural expression of pro-autophagic Ambra-1 as a prognostic biomarker for melanoma", Journal of Investigative Dermatology (2013), vol. 133, Supplement 1, p. S232, (May 2013), S232.

(Continued)

*Primary Examiner* — Michael Allen
(74) *Attorney, Agent, or Firm* — Schwegman Lundberg & Woessner, P.A.

(57) ABSTRACT

The present invention relates inter alia to therapeutic agents for use in the treatment of melanoma, methods of diagnosing an increased risk of metastasis in a subject suffering from melanoma, methods of treating such subjects, diagnostic assays and kits. More particularly, in certain embodiments the invention relates to identifying whether a subject suffering from melanoma has an increased risk of metastasis by determining the expression of Ambra-1 and Loricrin in a tissue sample obtained from the subject.

4 Claims, 12 Drawing Sheets

Specification includes a Sequence Listing.

(56) References Cited

OTHER PUBLICATIONS

Whitaker, S., et al., "Proautophagic Ambra-1 as biomarker of differentiation in cutaneous squamous carcinoma", Abstract: British Journal of Dermatology (2014) 170, ppe6-e40, (Apr. 2014), 1 pg.
"Chinese Application No. 201580061109.9, Search Report dated Aug. 13, 2018", (Aug. 13, 2018), 3 pgs.
Mocellin, Simone, et al., "Interferon Alpha Adjuvant Therapy in Patients With High-Risk Melanoma: A Systematic Review and Meta-analysis", JNCI, vol. 102, Issue 7, (Feb. 23, 2010), 493-501.

* cited by examiner

Figure 1
A
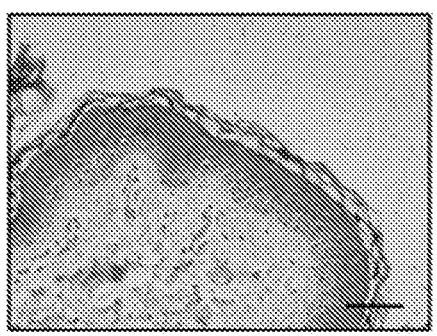
B
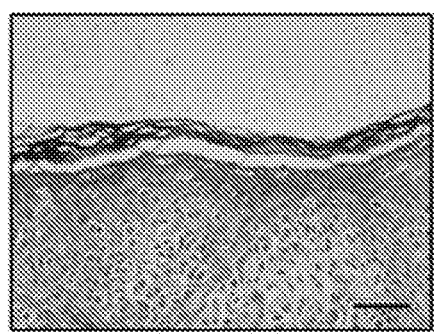
C
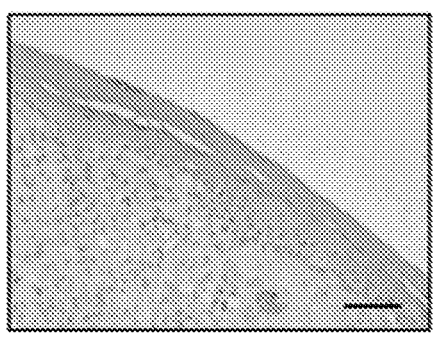
D
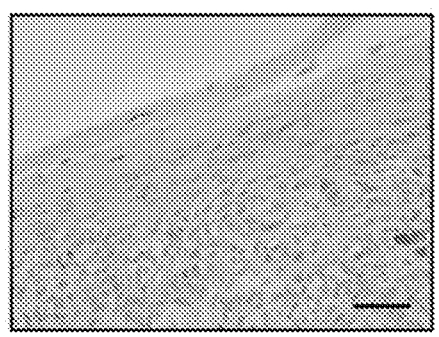

Figure 6

```
MKVVPEKNAV RILWGRERGA RAMGAQRLLQ ELVEDKTRWM KWEGKRVELP   50
DSPRSTFLLA FSPDRTLLAS THVNHNIYIT EVKTGKCVHS LIGHRRTPWC  100
VTFHPTISGL IASGCLDGEV RIWDLHGGSE SWFTDSNNAI ASLAFHPTAQ  150
LLLIATANEI HFWDWSRREP FAVVKTASEM ERVRLVRFDP LGHYLLTAIV  200
NPSNQQGDDE PEIPIDGTEL SHYRQRALLQ SQPVRRTPLL HNFLHMLSSR  250
SSGIQVGEQS TVQDSATPSP PPPPPQPSTE RPRTSAYIRL RQRVSYPTAE  300
CCQHLGILCL CSRCSGTRVP SLLPHQDSVP PASARATTPS FSFVQTEPFH  350
PPEQASSTQQ DQGLLNRPSA FSTVQSSTAG NTLRNLSLGP TRRSLGGPLS  400
SHPSRYHREI APGLTGSEWT RTVLSLNSRS EAESMPPPRT SASSVSLLSV  450
LRQQEGGSQA SVYTSATEGR GFPASGLATE SDGGNGSSQN NSGSIRHELQ  500
CDLRRFFLEY DRLQELDQSL SGEAPQTQQA QEMLNNNIES ERPGPSHQPT  550
PHSSENNSNL SRGHLNRCRA CHNLLTFNND TLRWERTTPN YSSGEASSSW  600
QVPSSFESVP SSGSQLPPLE RTEGQTPSSS RLELSSSASP QEERTVGVAF  650
NQETGHWERI YTQSSRSGTV SQEALHQDMP EESSEEDSLR RRLLESSLIS  700
LSRYDGAGSR EHPIYPDPAR LSPAAYYAQR MIQYLSRRDS IRQRSMRYQQ  750
NRLRSSTSSS SSDNQGPSVE GTDLEFEDFE DNGDRSRHRA PRNARMSAPS  800
LGRFVPRRFL LPEYLPYAGI FHERGQPGLA THSSVNRVLA GAVIGDGQSA  850
VASNIANTTY RLQWWDFTKF DLPEISNASV NVLVQNCKIY NDASCDISAD  900
GQLLAAFIPS SQRGFPDEGI LAVYSLAPHN LGEMLYTKRF GPNAISVSLS  950
PMGRYVMVGL ASRRILLHPS TEHMVAQVFR LQQAHGGETS MRRVFNVLYP 1000
MPADQRRHVS INSARWLPEP GLGLAYGTNK GDLVICRPEA LNSGVEYYWD 1050
QLNETVFTVH SNSRSSERPG TSRATWRTDR DMGLMNAIGL QPRNPATSVT 1100
SQGTQTLALQ LQNAETQTER EVPEPGTAAS GPGEGEGSEY GASGEDALSR 1150
IQRLMAEGGM TAVVQREQST TMASMGGFGN NIIVSHRIHR SSQTGTEPGA 1200
AHTSSPQPST SRGLLPEAGQ LAERGLSPRT ASWDQPGTPG REPTQPTLPS 1250
SSPVPIPVSL PSAEGPTLHC ELTNNNHLLD GGSSRGDAAG PRGEPRNR   1298
```

Figure 7

```
MSYQKKQPTP QPPVDCVKTS GGGGGGGGSG GGGCGFFGGG GSGGGSSGSG    50
CGYSGGGGYS GGGCGGGSSG GGGGGGIGGC GGGSGGSVKY SGGGGSSGGG   100
SGCFSSGGGG SGCFSSGGGG SSGGGSGCFS SGGGGSSGGG SGCFSSGGGG   150
FSGQAVQCQS YGGVSSGGSS GGGSGCFSSG GGGGSVCGYS GGGSGCGGGS   200
SGGSGSGYVS SQQVTQTSCA PQPSYGGGSS GGGGSGGSGC FSSGGGGGSS   250
GCGGGSSGIG SGCIISGGGS VCGGGSSGGG GGGSSVGGSG SGKGVPICHQ   300
TQQKQAPTWP SK                                           312
```

Fig. 8
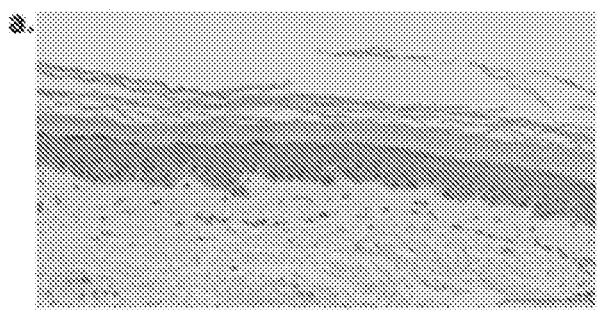
a.
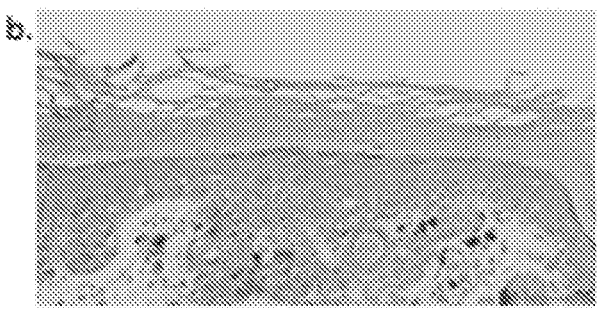
b.
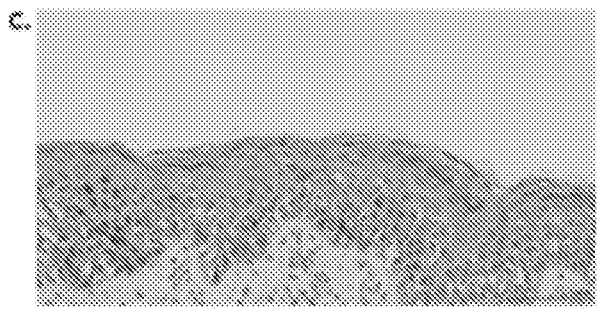
c.
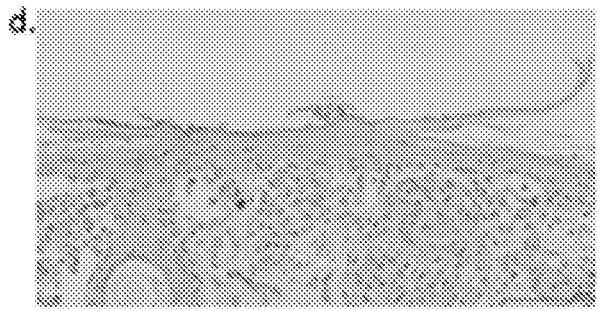
d.

SEQUENCE LISTING

<160> NUMBER OF SEQ ID NOS: 2

<210> SEQ ID NO 1
<211> LENGTH: 1298
<212> TYPE: PRT
<213> ORGANISM: Homo Sapiens

<400> SEQUENCE: 1

Met Lys Val Val Pro Glu Lys Asn Ala Val Arg Ile Leu Trp Gly Arg
1               5                   10                  15

Glu Arg Gly Ala Arg Ala Met Gly Ala Gln Arg Leu Leu Gln Glu Leu
            20                  25                  30

Val Glu Asp Lys Thr Arg Trp Met Lys Trp Glu Gly Lys Arg Val Glu
        35                  40                  45

Leu Pro Asp Ser Pro Arg Ser Thr Phe Leu Leu Ala Phe Ser Pro Asp
    50                  55                  60

Arg Thr Leu Leu Ala Ser Thr His Val Asn His Asn Ile Tyr Ile Thr

-continued

```
                65                  70                  75                  80
        Glu Val Lys Thr Gly Lys Cys Val His Ser Leu Ile Gly His Arg Arg
                            85                  90                  95
        Thr Pro Trp Cys Val Thr Phe His Pro Thr Ile Ser Gly Leu Ile Ala
                           100                 105                 110
        Ser Gly Cys Leu Asp Gly Glu Val Arg Ile Trp Asp Leu His Gly Gly
                           115                 120                 125
        Ser Glu Ser Trp Phe Thr Asp Ser Asn Asn Ala Ile Ala Ser Leu Ala
                           130                 135                 140
        Phe His Pro Thr Ala Gln Leu Leu Ile Ala Thr Ala Asn Glu Ile
        145                 150                 155                 160
        His Phe Trp Asp Trp Ser Arg Arg Glu Pro Phe Ala Val Val Lys Thr
                           165                 170                 175
        Ala Ser Glu Met Glu Arg Val Arg Leu Val Arg Phe Asp Pro Leu Gly
                           180                 185                 190
        His Tyr Leu Leu Thr Ala Ile Val Asn Pro Ser Asn Gln Gln Gly Asp
                           195                 200                 205
        Asp Glu Pro Glu Ile Pro Ile Asp Gly Thr Glu Leu Ser His Tyr Arg
        210                 215                 220
        Gln Arg Ala Leu Leu Gln Ser Gln Pro Val Arg Arg Thr Pro Leu Leu
        225                 230                 235                 240
        His Asn Phe Leu His Met Leu Ser Ser Arg Ser Ser Gly Ile Gln Val
                           245                 250                 255
        Gly Glu Gln Ser Thr Val Gln Asp Ser Ala Thr Pro Ser Pro Pro Pro
                           260                 265                 270
        Pro Pro Pro Gln Pro Ser Thr Glu Arg Pro Arg Thr Ser Ala Tyr Ile
                           275                 280                 285
        Arg Leu Arg Gln Arg Val Ser Tyr Pro Thr Ala Glu Cys Cys Gln His
                           290                 295                 300
        Leu Gly Ile Leu Cys Leu Cys Ser Arg Cys Ser Gly Thr Arg Val Pro
        305                 310                 315                 320
        Ser Leu Leu Pro His Gln Asp Ser Val Pro Pro Ala Ser Ala Arg Ala
                           325                 330                 335
        Thr Thr Pro Ser Phe Ser Phe Val Gln Thr Glu Pro Phe His Pro Pro
                           340                 345                 350
        Glu Gln Ala Ser Ser Thr Gln Gln Asp Gln Gly Leu Leu Asn Arg Pro
                           355                 360                 365
        Ser Ala Phe Ser Thr Val Gln Ser Ser Thr Ala Gly Asn Thr Leu Arg
                           370                 375                 380
        Asn Leu Ser Leu Gly Pro Thr Arg Arg Ser Leu Gly Pro Leu Ser
        385                 390                 395                 400
        Ser His Pro Ser Arg Tyr His Arg Glu Ile Ala Pro Gly Leu Thr Gly
                           405                 410                 415
        Ser Glu Trp Thr Arg Thr Val Leu Ser Leu Asn Ser Arg Ser Glu Ala
                           420                 425                 430
        Glu Ser Met Pro Pro Arg Thr Ser Ala Ser Ser Val Ser Leu Leu
                           435                 440                 445
        Ser Val Leu Arg Gln Gln Glu Gly Gly Ser Gln Ala Ser Val Tyr Thr
                           450                 455                 460
        Ser Ala Thr Glu Gly Arg Gly Phe Pro Ala Ser Gly Leu Ala Thr Glu
        465                 470                 475                 480
        Ser Asp Gly Gly Asn Gly Ser Ser Gln Asn Asn Ser Gly Ser Ile Arg
                           485                 490                 495
```

```
His Glu Leu Gln Cys Asp Leu Arg Arg Phe Leu Glu Tyr Asp Arg
            500                 505                 510
Leu Gln Glu Leu Asp Gln Ser Leu Ser Gly Glu Ala Pro Gln Thr Gln
            515                 520                 525
Gln Ala Gln Glu Met Leu Asn Asn Ile Glu Ser Glu Arg Pro Gly
530                 535                 540
Pro Ser His Gln Pro Thr Pro His Ser Glu Asn Asn Ser Asn Leu
545                 550                 555                 560
Ser Arg Gly His Leu Asn Arg Cys Arg Ala Cys His Asn Leu Leu Thr
                565                 570                 575
Phe Asn Asn Asp Thr Leu Arg Trp Glu Arg Thr Thr Pro Asn Tyr Ser
            580                 585                 590
Ser Gly Glu Ala Ser Ser Ser Trp Gln Val Pro Ser Ser Phe Glu Ser
            595                 600                 605
Val Pro Ser Ser Gly Ser Gln Leu Pro Pro Leu Glu Arg Thr Glu Gly
            610                 615                 620
Gln Thr Pro Ser Ser Ser Arg Leu Glu Leu Ser Ser Ser Ala Ser Pro
625                 630                 635                 640
Gln Glu Glu Arg Thr Val Gly Val Ala Phe Asn Gln Glu Thr Gly His
                645                 650                 655
Trp Glu Arg Ile Tyr Thr Gln Ser Ser Arg Ser Gly Thr Val Ser Gln
                660                 665                 670
Glu Ala Leu His Gln Asp Met Pro Glu Glu Ser Ser Glu Glu Asp Ser
            675                 680                 685
Leu Arg Arg Arg Leu Leu Glu Ser Ser Leu Ile Ser Leu Ser Arg Tyr
            690                 695                 700
Asp Gly Ala Gly Ser Arg Glu His Pro Ile Tyr Pro Asp Pro Ala Arg
705                 710                 715                 720
Leu Ser Pro Ala Ala Tyr Tyr Ala Gln Arg Met Ile Gln Tyr Leu Ser
                725                 730                 735
Arg Arg Asp Ser Ile Arg Gln Arg Ser Met Arg Tyr Gln Gln Asn Arg
            740                 745                 750
Leu Arg Ser Ser Thr Ser Ser Ser Ser Asp Asn Gln Gly Pro Ser
            755                 760                 765
Val Glu Gly Thr Asp Leu Glu Phe Glu Asp Phe Glu Asp Asn Gly Asp
            770                 775                 780
Arg Ser Arg His Arg Ala Pro Arg Asn Ala Arg Met Ser Ala Pro Ser
785                 790                 795                 800
Leu Gly Arg Phe Val Pro Arg Arg Phe Leu Leu Pro Glu Tyr Leu Pro
                805                 810                 815
Tyr Ala Gly Ile Phe His Glu Arg Gly Gln Pro Gly Leu Ala Thr His
                820                 825                 830
Ser Ser Val Asn Arg Val Leu Ala Gly Ala Val Ile Gly Asp Gly Gln
            835                 840                 845
Ser Ala Val Ala Ser Asn Ile Ala Asn Thr Thr Tyr Arg Leu Gln Trp
            850                 855                 860
Trp Asp Phe Thr Lys Phe Asp Leu Pro Glu Ile Ser Asn Ala Ser Val
865                 870                 875                 880
Asn Val Leu Val Gln Asn Cys Lys Ile Tyr Asn Asp Ala Ser Cys Asp
                885                 890                 895
Ile Ser Ala Asp Gly Gln Leu Leu Ala Ala Phe Ile Pro Ser Ser Gln
            900                 905                 910
```

```
Arg Gly Phe Pro Asp Glu Gly Ile Leu Ala Val Tyr Ser Leu Ala Pro
    915                 920                 925

His Asn Leu Gly Glu Met Leu Tyr Thr Lys Arg Phe Gly Pro Asn Ala
    930                 935                 940

Ile Ser Val Ser Leu Ser Pro Met Gly Arg Tyr Val Met Val Gly Leu
945                 950                 955                 960

Ala Ser Arg Arg Ile Leu Leu His Pro Ser Thr Glu His Met Val Ala
                965                 970                 975

Gln Val Phe Arg Leu Gln Gln Ala His Gly Gly Glu Thr Ser Met Arg
            980                 985                 990

Arg Val Phe Asn Val Leu Tyr Pro Met Pro Ala Asp Gln Arg Arg His
        995                 1000                1005

Val Ser Ile Asn Ser Ala Arg Trp Leu Pro Glu Pro Gly Leu Gly
    1010                1015                1020

Leu Ala Tyr Gly Thr Asn Lys Gly Asp Leu Val Ile Cys Arg Pro
    1025                1030                1035

Glu Ala Leu Asn Ser Gly Val Glu Tyr Tyr Trp Asp Gln Leu Asn
    1040                1045                1050

Glu Thr Val Phe Thr Val His Ser Asn Ser Arg Ser Ser Glu Arg
    1055                1060                1065

Pro Gly Thr Ser Arg Ala Thr Trp Arg Thr Asp Arg Asp Met Gly
    1070                1075                1080

Leu Met Asn Ala Ile Gly Leu Gln Pro Arg Asn Pro Ala Thr Ser
    1085                1090                1095

Val Thr Ser Gln Gly Thr Gln Thr Leu Ala Leu Gln Leu Gln Asn
    1100                1105                1110

Ala Glu Thr Gln Thr Glu Arg Glu Val Pro Glu Pro Gly Thr Ala
    1115                1120                1125

Ala Ser Gly Pro Gly Glu Gly Glu Gly Ser Glu Tyr Gly Ala Ser
    1130                1135                1140

Gly Glu Asp Ala Leu Ser Arg Ile Gln Arg Leu Met Ala Glu Gly
    1145                1150                1155

Gly Met Thr Ala Val Val Gln Arg Glu Gln Ser Thr Thr Met Ala
    1160                1165                1170

Ser Met Gly Gly Phe Gly Asn Asn Ile Ile Val Ser His Arg Ile
    1175                1180                1185

His Arg Ser Ser Gln Thr Gly Thr Glu Pro Gly Ala Ala His Thr
    1190                1195                1200

Ser Ser Pro Gln Pro Ser Thr Ser Arg Gly Leu Leu Pro Glu Ala
    1205                1210                1215

Gly Gln Leu Ala Glu Arg Gly Leu Ser Pro Arg Thr Ala Ser Trp
    1220                1225                1230

Asp Gln Pro Gly Thr Pro Gly Arg Glu Pro Thr Gln Pro Thr Leu
    1235                1240                1245

Pro Ser Ser Ser Pro Val Pro Ile Pro Val Ser Leu Pro Ser Ala
    1250                1255                1260

Glu Gly Pro Thr Leu His Cys Glu Leu Thr Asn Asn Asn His Leu
    1265                1270                1275

Leu Asp Gly Gly Ser Ser Arg Gly Asp Ala Ala Gly Pro Arg Gly
    1280                1285                1290

Glu Pro Arg Asn Arg
    1295
```

```
<210> SEQ ID NO 2
<211> LENGTH: 312
<212> TYPE: PRT
<213> ORGANISM: Homo Sapiens

<400> SEQUENCE: 2

Met Ser Tyr Gln Lys Lys Gln Pro Thr Pro Gln Pro Pro Val Asp Cys
1               5                   10                  15

Val Lys Thr Ser Gly Gly Gly Gly Gly Gly Gly Ser Gly Gly Gly
            20                  25                  30

Gly Cys Gly Phe Phe Gly Gly Gly Ser Gly Gly Gly Ser Ser Gly
            35                  40                  45

Ser Gly Cys Gly Tyr Ser Gly Gly Gly Tyr Ser Gly Gly Gly Cys
    50                  55                  60

Gly Gly Gly Ser Ser Gly Gly Gly Gly Gly Ile Gly Gly Cys
65                  70                  75                  80

Gly Gly Gly Ser Gly Gly Ser Val Lys Tyr Ser Gly Gly Gly Ser
                85                  90                  95

Ser Gly Gly Gly Ser Gly Cys Phe Ser Ser Gly Gly Gly Ser Gly
            100                 105                 110

Cys Phe Ser Ser Gly Gly Gly Ser Ser Gly Gly Gly Ser Gly Cys
            115                 120                 125

Phe Ser Ser Gly Gly Gly Gly Ser Ser Gly Gly Gly Ser Gly Cys Phe
    130                 135                 140

Ser Ser Gly Gly Gly Gly Phe Ser Gly Gln Ala Val Gln Cys Gln Ser
145                 150                 155                 160

Tyr Gly Gly Val Ser Ser Gly Gly Ser Ser Gly Gly Gly Ser Gly Cys
                165                 170                 175

Phe Ser Ser Gly Gly Gly Gly Gly Ser Val Cys Gly Tyr Ser Gly Gly
            180                 185                 190

Gly Ser Gly Cys Gly Gly Gly Ser Ser Gly Gly Ser Gly Ser Gly Tyr
    195                 200                 205

Val Ser Ser Gln Gln Val Thr Gln Thr Ser Cys Ala Pro Gln Pro Ser
    210                 215                 220

Tyr Gly Gly Gly Ser Ser Gly Gly Gly Gly Ser Gly Gly Ser Gly Cys
225                 230                 235                 240

Phe Ser Ser Gly Gly Gly Gly Gly Ser Ser Gly Cys Gly Gly Gly Ser
            245                 250                 255

Ser Gly Ile Gly Ser Gly Cys Ile Ile Ser Gly Gly Gly Ser Val Cys
            260                 265                 270

Gly Gly Gly Ser Ser Gly Gly Gly Gly Gly Gly Ser Ser Val Gly Gly
            275                 280                 285

Ser Gly Ser Gly Lys Gly Val Pro Ile Cys His Gln Thr Gln Gln Lys
            290                 295                 300

Gln Ala Pro Thr Trp Pro Ser Lys
305                 310
```

AMBRA-1 AND LORICRIN AS BIOMARKERS FOR DISEASE PROGRESSION IN MELANOMA

PRIORITY CLAIM TO RELATED APPLICATIONS

This application is a U.S. national stage application filed under 35 U.S.C. § 371 from International Application Serial No. PCT/GB2015/053347, which was filed 5 Nov. 2015, and published as WO2016/075440 on 19 May 2016, and which claims priority to United Kingdom Application No. 1419976.4, filed 10 Nov. 2014, which applications and publication are incorporated by reference as if reproduced herein and made a part hereof in their entirety, and the benefit of priority of each of which is claimed herein.

FIELD OF THE INVENTION

The present invention relates inter alia to therapeutic agents for use in the treatment of melanoma, methods of diagnosing an increased risk of metastasis in a subject suffering from melanoma, methods of treating such subjects, diagnostic assays and kits. More particularly, in certain embodiments the invention relates to identifying whether a subject suffering from melanoma has an increased risk of metastasis by determining the expression of Ambra-1 and Loricrin in a tissue sample obtained from the subject.

BACKGROUND TO THE INVENTION

Melanoma is responsible for only 2.3% of all skin cancers, but it is the most life threatening form, being responsible for over 75% of skin cancer deaths. Cutaneous melanoma is currently a major public health concern due to rising incident rates worldwide, claiming the lives of more than 2000 individuals in the UK alone each year. The rate of increase is higher than for any other cancer and it has been likened to an epidemic. Some of the increase may be due to improvements in surveillance and early detection as well as changes in diagnostic criteria, however, it is considered that a substantial proportion of the increase is real. The increase has been linked to a rise in sun exposure and/or increased used of artificial sunbeds.

European age-standardized incident rates have increased 4-fold for woman and 7-fold for men over the last 30 years. Melanoma is now the fifth most common cancer in the UK, accounting for 4% of all new cancer cases. Mortality rates have also increased, but at a rate disproportionately less than incidence, such that the ratio of deaths to patient cases as fallen steadily over the last 50 years. Even so, melanoma accounts for nearly 50,000 deaths annually, worldwide.

Factors that affect prognosis include the thickness of the tumor in millimeters (Breslow's depth), the depth related to skin structures (Clark level), the type of melanoma, the presence of metastasis and the presence of ulceration. Primary melanomas which demonstrate epidermal ulceration at the time of diagnosis predicts increased rates of metastasis and poorer outcomes compared to non-ulcerated tumours. However, the underlying biology of ulceration remains enigmatic.

Treatment of early stage (AJCC stage 1a or 1b) melanoma involves the removal of the tissue surrounding the melanoma, known as a wide local excision. This is typically followed by regular examination of the patient for the recurrence of disease over a period of 1-5 years. Therapy, such as chemotherapy, is not given to patients with early stage melanoma.

For patients with thicker tumours (AJCC stage 2a, 2b or 2c) a wide local excision may be followed by a sentinel lymph node biopsy to determine whether the disease has spread to the lymph nodes. If it has, a lymph node dissection may be performed. Treatment after surgery to help prevent the melanoma from returning or spreading is known as adjuvant therapy. Adjuvant therapy may be chemotherapy or biological therapy (e.g. interferon treatment). However, adjuvant therapy is generally only offered to patients with stage 2 melanoma as part of a clinical trial.

Chemotherapy, radiotherapy and/or biological therapy may be used to treat recurring melanomas in patients who have had a stage 2 tumour removed, to help control further metastatic progression in patients with disease confined to lymph nodes (stage 3) or to shrink melanomas in patients with advanced metastatic disease (AJCC stage 4) in order to reduce symptoms.

There remains a need to improve treatment of patients suffering from melanoma and to decrease the likelihood of progression to metastasis.

It is an aim of some embodiments of the present invention to at least partially mitigate some of the problems identified in the prior art.

SUMMARY OF CERTAIN EMBODIMENTS OF THE INVENTION

According to a first aspect of the present invention, there is provided a therapeutic agent for use in the treatment of melanoma in a subject, wherein said subject has been identified as having decreased or a loss of expression of Ambra-1 and Loricrin in a tissue sample obtained from the subject.

Ambra-1 (activating molecule in Beclin-1 regulated autophagy protein 1) is a WD40-containing protein. Studies have implicated Ambra-1 in the control of autophagy, in which Ambra-1 is believed to function as a protein-protein interacting platform. The main role of Ambra-1 during autophagy is thought to be as a member of the Beclin-1/VPS34 complex which is involved in the formation of PI3K rich membranes during the nucleation phase of autophagy. Studies have suggested that Ambra-1 also acts directly as an upstream regulator of autophagic activity. The amino acid sequence of Ambra-1 is shown in the Figures.

Ambra-1 has additionally been shown to play a role in cellular differentiation. Functional inactivation of Ambra-1 in a mouse model led to lethality in utero with severe neural tube defects associated with autophagic impairment and unbalanced cellular proliferation. Conversely, over expression of Ambra-1 has been shown to decrease cellular proliferation rates in neural tissue, thus supporting its role as a key player in epithelial proliferation.

Loricrin is a glycine-serine-cysteine-rich protein which, in humans, is encoded by the LOR gene. The LOR gene is part of a cluster of genes on chromosome 1 called the epidermal differentiation complex. These genes are involved in the formation and maintenance of the outer layer of skin (the epidermis), particularly its tough outer surface (the stratum corneum). The stratum corneum, which is formed in a process known as cornification, provides a sturdy barrier between the body and its environment. Each cell of the stratum corneum, called a corneocyte, is surrounded by a protein shell called a cornified envelope (CE). Loricrin is the predominant protein of the cornified envelope. Links between Loricrin and other components of the envelopes hold the corneocytes together and help give the stratum corneum its strength. The amino acid sequence of Loricrin is shown in the Figures.

According to a second aspect of the present invention, there is provided a therapeutic agent for use in the treatment of melanoma in a subject, wherein said subject has been identified as having an increased risk of metastasis, wherein identification of the increased risk is determined by:
  (i) determining the expression of Ambra-1 and Loricrin in a tissue sample obtained from the subject, wherein the tissue sample comprises tissue overlying a primary melanoma; and
  (ii) comparing the expression obtained in (i) with a reference tissue or levels obtained therefrom;
wherein a decrease in the expression of Ambra-1 and Loricrin in the tissue sample compared to the reference tissue or levels or a loss of expression of Ambra-1 and Loricrin in the tissue sample is indicative of an increased risk of metastasis in the subject.

It will be appreciated that, in some embodiments, comparison of the expression of Ambra-1 and Loricrin in the tissue sample with a reference may not be required, for example where a loss of expression is determined. Thus, in certain embodiments, a decrease or loss of expression of Ambra-1 and Loricrin is apparent without having to compare the expression to a reference tissue.

According to a third aspect of the present invention, there is provided a therapeutic agent for use to prevent or reduce the likelihood of progression to metastasis in a subject suffering from melanoma and who has been identified as being at increased risk of progressing to metastasis, wherein said identification comprises determining that the subject has decreased or a loss of expression of Ambra-1 and Loricrin in keratinocytes overlying a primary melanoma of the subject.

According to a fourth aspect of the present invention, there is provided an in vitro method for determining whether a subject with melanoma has an increased risk of metastasis, the method comprising:
  (i) determining the expression of Ambra-1 and Loricrin in a tissue sample obtained from the subject, wherein the tissue sample comprises tissue overlying a primary melanoma; and
  (ii) comparing the expression obtained in (i) with a reference tissue or levels obtained therefrom,
wherein a decrease in the expression of Ambra-1 and Loricrin in the tissue sample compared to the reference tissue or levels or a loss of expression of Ambra-1 and Loricrin in the tissue sample is indicative of an increased risk of metastasis.

According to a fifth aspect of the present invention, there is provided a method of determining a treatment regime for a subject suffering from melanoma, the method comprising:
  a) obtaining a tissue sample from the subject, wherein the tissue sample comprises tissue overlying a primary melanoma;
  b) determining the expression of Ambra-1 and Loricrin in the tissue sample;
  c) comparing the expression obtained in (b) with a reference tissue or levels obtained therefrom, and
  d) (i) if expression of Ambra-1 and Loricrin is normal or increased, following a normal recognized care pathway, or
  (ii) if expression of Ambra-1 and Loricrin is decreased or lost, treating the subject with a systemic anti-cancer treatment regime.

According to a sixth aspect of the present invention, there is provided a method of treating a subject suffering from melanoma, the method comprising administering a therapeutic agent to the subject, wherein the subject has been identified as having decreased or a loss of expression of Ambra-1 and Loricrin in a tissue sample obtained from the subject.

According to a seventh aspect of the present invention, there is provided a method of treating a subject suffering from melanoma, the method comprising:
  (i) determining the expression of Ambra-1 and Loricrin in a tissue sample obtained from the subject, wherein the tissue sample comprises tissue overlying a primary melanoma;
  (ii) comparing the expression obtained in (i) with a reference tissue or levels obtained therefrom, and
if there is a decrease in the expression of Ambra-1 and Loricrin in the tissue sample compared to the reference tissue or levels, or a loss of expression of Ambra-1 and Loricrin in the tissue sample, administering a therapeutic agent to the subject.

According to an eighth aspect of the present invention, there is provided an in vitro assay for predicting an increased risk of metastasis of a subject suffering from melanoma, the assay comprising:
  (i) contacting a tissue sample obtained from the subject with a first ligand specific for Ambra-1, wherein the presence of Ambra-1 creates an Ambra-1-ligand complex;
  (ii) contacting the tissue sample with a second ligand specific for Loricrin, wherein the presence of Loricrin creates a Loricrin-ligand complex; and
  (iii) detecting and/or quantifying the Ambra-1-ligand complex and the Loricrin-ligand complex.

The subject may be a human or an animal suffering from melanoma. In some embodiments, the subject is a human patient. In some embodiments, the subject has already been diagnosed as having melanoma.

In some embodiments the subject is suffering from AJCC stage 1, stage 2, stage 3 or stage 4 melanoma. In some embodiments, the subject is suffering from AJCC stage 1a, stage 1b, stage 2a, stage 2b or stage 2c melanoma. In some embodiments, the subject is suffering from AJCC stage 1a or stage 1b melanoma. In some embodiments, the methods described herein further comprise staging a primary tumour present in a tissue sample obtained from a subject in accordance with AJCC staging.

Treatment for early stage melanoma typically involves surgery to excise the tumour(s). Therapy is generally used to control the spread of metastases in the later stages of the disease, by which time the prognosis is typically poor. The identification of those subjects who are in the early stages of the disease but who are at a high or increased risk of metastasis would advantageously enable treatment to be tailored accordingly. For example, therapy could be administered to those subjects sooner than it might normally be administered, thereby inhibiting, preventing or delaying metastasis and improving the prognosis of those subject.

Thus, in some embodiments, the subject, prior to identification, is ineligible for therapeutic agent treatment. In certain embodiments, a subject can be put forward for a treatment regime at an earlier or less progressed stage as compared to the prior art methods of treating melanoma in which a patient is only treated with a therapeutic agent when they are suffering from AJCC stage 3 or 4 melanoma, or recurrence of disease after AJCC stage 2 or 3 melanoma.

In some embodiments, the subject has an ulcerated melanoma.

Unexpectedly, the present inventors have identified a correlation between the expression levels of both Ambra-1 and Loricrin and the likelihood of metastasis in a subject with melanoma. In particular, it is considered that a decrease in the level of expression, or a loss of expression, of both Ambra-1 and Loricrin indicates that the subject has an increased risk of metastasis.

As used herein, a decrease or loss in the expression of Ambra-1 and Loricrin will be understood as meaning that the level of expression of both Ambra-1 and Loricrin is less than about 75% of the respective reference level.

In some embodiments, a decrease in expression of Ambra-1 and Loricrin will be understood as meaning that the level of expression of both Ambra-1 and Loricrin is from about 25 to about 75% of the respective reference level. In some embodiments, a loss of expression of Ambra-1 and Loricrin will be understood as meaning that the level of expression of both Ambra-1 and Loricrin is less than about 25% of the reference level of the relevant protein. Normal expression is understood to mean that the expression of both Ambra-1 and Loricrin is greater than about 75% of the respective reference level.

Thus, in some embodiments, the expression level of Ambra-1 in the tissue sample is from about 25% to about 75% of the reference level. In some embodiments, the expression level of Ambra-1 is no greater than 75%, no greater than 70%, no greater than 60%, no greater than 50%, no greater than 40% or no greater than 30% of the reference level.

In some embodiments, the expression level of Loricrin in the tissue sample is from about 25% to about 75% of the reference level. In some embodiments, the expression level of Loricrin is no greater than 75%, no greater than 70%, no greater than 60%, no greater than 50%, no greater than 40% or no greater than 30% of the reference level.

In some embodiments, there is substantially no expression of Ambra-1 and/or Loricrin in the tissue sample. In certain embodiments, the expression of Ambra-1 and/or Loricrin is less than 25%.

In some embodiments, an increased risk of metastasis means a 7-year metastasis-free (also known as "disease-free") survival rate of less than 50%, for example less than 40%, for example less than 30%, for example less than 20%, for example less than 10% or less than 5% for example.

Accordingly, Ambra-1 and Loricrin can be considered to be biomarkers for disease progression of melanoma to metastasis. Thus, embodiments of the present invention may be considered as providing methods for predicting the progression of melanoma to metastasis in a subject. In some embodiments, the present invention further provides the use of Ambra-1 and Loricrin, in a tissue sample comprising tissue overlying a primary melanoma, as prognostic biomarkers for disease progression of melanoma to metastasis. Aptly, Ambra-1 and Loricrin can be considered to be biomarkers for stratifying subjects with melanoma into those more likely to develop metastasis and those less likely to develop metastasis. Advantageously, the methods of certain embodiments of the invention help to identify which subjects with melanoma are most likely to benefit from treatment with a therapeutic agent. Aptly, certain embodiments of the present invention may enable treatment with a therapeutic agent for a patient who would otherwise not have been eligible for treatment with a therapeutic agent.

Rather than determining the expression levels of biomarkers in the tumour itself, the methods of certain embodiments of the invention comprise determining the expression levels of Ambra-1 and Loricrin in tissue overlying a primary melanoma. Without being bound by theory, it is thought that reduced or loss of expression of these proteins may indicate a breakdown of the epidermis overlying, and the endothelial tissue lining blood vessel or lymphatics underlying, the tumour, suggesting that cancer cells may be able to, or may have already, migrated from the primary tumour. Such migration may lead to metastasis.

In some embodiments, the tissue sample comprises tissue overlying a primary melanoma. In some embodiments, the tissue sample comprises at least a portion of the peritumoural epidermis overlying the primary melanoma. In some embodiments, the tissue sample further comprises a portion of normal tissue adjacent to the primary melanoma. In some embodiments, the portion of normal tissue provides a reference. Aptly, the reference is a reference tissue and/or provides a reference level of Ambra-1 and Loricrin.

In some embodiments, the method comprises determining the expression levels of Ambra-1 and Loricrin in the epidermis. Keratinocytes are cells which constitute about 90% of the epidermis. Thus, in some embodiments, the tissue sample comprises keratinocytes overlying the primary melanoma. Aptly, the subject may be identified as being at increased risk of metastasis, wherein said identification comprises determining that the subject has a decrease or loss of expression of Ambra-1 and Loricrin in keratinocytes overlying the primary melanoma of the subject.

In some embodiments, the tissue sample has previously been obtained from the subject such that the sampling itself does not form a part of the methods of the invention. The sample may have been obtained immediately prior to the method, or a number of hours, days or weeks prior to the method. In other embodiments, a method of the invention may additionally comprise the step of obtaining the tissue sample from the subject.

Aptly, the expression of Ambra-1 and Loricrin in the tissue sample is compared to one or more references. Aptly, the reference is a tissue, or levels of expression obtained therefrom.

In some embodiments, the reference comprises levels of Ambra-1 and Loricrin expression that are characteristic of normal tissue. Aptly, reference levels of Loricrin and Ambra-1 may be obtained by determining the expression of Loricrin and Ambra-1 in a reference tissue. In some embodiments, the expression levels of Loricrin and Ambra-1 in a reference tissue are determined by visual or automated assessment.

In some embodiments, reference levels of Ambra-1 and Loricrin expression that are characteristic of normal tissue are obtained by determining expression levels in tissue samples obtained from one or more (e.g. a cohort) of healthy subjects.

In some embodiments, the reference tissue comprises normal tissue. In some embodiments, the normal tissue comprises epidermis from a site which does not include a primary melanoma. In some embodiments, the reference tissue (or levels obtained therefrom) is an internal reference (i.e. obtained from the subject). In some embodiments, the reference tissue is normal tissue obtained from a site adjacent to the primary melanoma. In other embodiments, the reference tissue is obtained from a site of the subject which is remote from the primary melanoma. Thus, in some embodiment, the reference level is the level of expression of Loricrin and/or Ambra-1 in normal tissue. The reference tissue is aptly taken from normal epidermis and the reference level is a level of expression in the keratinocytes of the normal epidermis. The expression of Ambra-1 and/or Loricrin in the reference tissue, for example to generate reference levels, can be determined using the methods described herein.

Aptly, the tissue sample may be a biopsy, or a section thereof, obtained from the subject. A tissue sample, such as a biopsy, can be obtained through a variety of sampling methods known to those skilled in the art, including a punch biopsy, shave biopsy, wide local excision and other means. Aptly, the tumour sample is taken from a surgical site from which the primary melanoma has been excised from a subject.

Aptly, the tissue sample may be frozen, fresh, fixed (e.g. formalin fixed), centrifuged, and/or embedded (e.g. paraffin embedded), etc. The tissue sample may be or have been subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the Ambra-1 and Loricrin in the sample. Likewise, biopsies may also be subjected to post-collection preparative and storage techniques, e.g., fixation. A tissue sample, or a section thereof, may be mounted on a solid support, such as a slide.

In some embodiments, determining the expression of Ambra-1 and Loricrin in the tissue sample comprises measuring the levels of each of the proteins present in the tissue sample. This may be achieved by methods known to those skilled in the art. Such methods include immunoassays, for example immunohistochemistry, ELISA, Western blots, immunoprecipitation followed by SDS-PAGE and immunocytochemistry, and the like.

Thus, in some embodiments, determining the expression levels of Ambra-1 and Loricrin comprises carrying out an assay. In some embodiments, the assay is an in vitro assay.

In some embodiments, the subject is identified as having an increased risk of metastasis by determining the expression of Ambra-1 and Loricrin in the tissue sample in a method comprising:

contacting the tissue sample with a first ligand specific for Ambra-1, wherein the presence of Ambra-1 creates an Ambra-1-ligand complex;
contacting the tissue sample with a second ligand specific for Loricrin, wherein the presence of Loricrin creates a Loricrin-ligand complex; and
detecting and/or quantifying the Ambra-1-ligand complex and the Loricrin-ligand complex.

In some embodiments, the first ligand comprises an anti-Ambra-1 antibody or aptamer. In some embodiments the anti-Ambra-1 antibody or aptamer binds specifically to a protein having the sequence shown in SEQ ID NO. 1.

In some embodiments, the second ligand comprises an anti-Loricrin antibody or aptamer. In some embodiments the anti-Loricrin antibody or aptamer binds specifically to a protein having the sequence shown in SEQ ID NO. 2.

The amino acid sequences of human Ambra-1 and Loricrin are provided herein as examples, however, it will be appreciated that variants of these sequences may be known or identified. In some embodiments, the subject is a non-human mammal. It should therefore also be appreciated that references herein to Ambra-1 (or SEQ ID NO. 1) and Loricrin (or SEQ ID NO. 2) include the sequences of non-human homologues thereof.

In some embodiments, the first and/or second ligand comprises a detection moiety (e.g. a fluorescent label). A detection moiety enables the direct or indirect detection and/or quantification of the complexes formed.

In some embodiments, the first ligand comprises a first detection moiety and the second ligand comprises a second detection moiety. The first detection moiety may be the same as the second detection moiety, or it may be different.

In some embodiments, the method comprises contacting a first portion or section of the tissue sample with the first ligand, and contacting a second portion or section of the tissue sample with the second ligand. This is particularly suitable for embodiments wherein the first detection moiety is the same as the second detection moiety. In some alternative embodiments, the method comprises contacting the tissue sample, or a portion or section thereof, with the first ligand and contacting the same tissue sample, or portion or section thereof, with the second ligand. It may be possible to detect and/or quantify both the Ambra-1-ligand complex and the Loricrin-ligand complex in the same sample, or portion or section thereof, particularly if the first and second detection moieties are different.

Aptly, the first and/or second ligands may be used in combination with one or more capture agents. Thus, in some embodiments, the step of detecting and/or quantifying the Ambra-1-ligand complex and the Loricrin-ligand complex comprises contacting the tissue sample(s) (or the section(s) or portion(s) thereof) with at least one capture agent. Aptly, a first capture agent which binds specifically to the first ligand may be used to detect and/or quantify the Ambra-1-ligand complex, while a second capture agent which binds specifically to the second ligand may be used to the detect and/or quantify the Loricrin-ligand complex. Alternatively, a single capture agent may be used which is capable of binding specifically to both the first and second ligands.

In some embodiments, the capture agent comprises a binding moiety and a detection moiety.

In some embodiments, the binding moiety is a secondary antibody which binds specifically to the first and/or second ligands. For example, the binding moiety may be a universal anti-IgG antibody that is capable of binding to primary antibodies used as the first and second ligands.

In some embodiments, the method further comprises one or more wash steps to remove unbound first and second ligands and, optionally, unbound capture agents.

In some particular embodiments, there is provided an in vitro assay for predicting an increased risk of metastasis in a subject suffering from melanoma, the assay comprising:

contacting a first portion of a tissue sample obtained from the subject with a first ligand specific for Ambra-1, wherein the presence of Ambra-1 creates an Ambra-1-ligand complex;
contacting a second portion of the tissue sample with a second ligand specific for Loricrin, wherein the presence of Loricrin creates a Loricrin-ligand complex;
washing the first and second portions of the tissue sample to remove unbound ligands;
contacting the first and second portions of the tissue sample with a capture agent,
wherein the capture agent comprises a detection moiety and a binding moiety specific for the first and second ligands;
washing the first and second portions of the tissue sample to remove unbound capture agent; and
detecting and/or quantifying the capture agent present in the first and second portions of the tissue sample.

Aptly, a suitable detection moiety is selected from a fluorescent moiety, a luminescent moiety, a bioluminescent moiety, a radioactive material, a colorimetric moiety, a nanoparticle having suitable detectable properties, a chromogenic moiety, biotin or an enzyme.

Suitable fluorescent moieties include fluorescent proteins (such as phycoerythrin (PE), peridininchlorophyll-protein complex (PerCP) and allophycocyanin (APC)) fluorescent dyes (such as Fluorescein Isothiocyanate (FITC), rhodamines (Rs) and cyanines (Cys)), fluorescent tandem complexes (such as Allophycocyanin-Cyanine 7 (APC-Cy7), Peridinin-Chlorophyll-Protein complex-Cyanine 5 (PerCP-cy5) and Phycoerythrin-TEXAS RED (PE-TexasRed)), and nanocrystals (such as QDOT® 525, QDOT® 545 and QDOT® 625). The presence of Ambra-1-ligand and Loricrin-ligand complexes can be detected using fluorescence microscopy via the use of fluorescent ligands or a capture agent comprising a fluorescent detection moiety.

In embodiments wherein the detection moiety comprises an enzyme, the presence of the Ambra-1-ligand complex and the Loricrin-ligand complex can be detected and/or quantified by detecting and/or quantifying the reaction product of a reaction of a substrate catalyzed by the enzyme. In these embodiments, the method further comprises adding a substrate of the enzyme and detecting and/or quantifying the product of the reaction performed on the substrate by the enzyme. For example, the reaction may result in the production of a coloured precipitate, which would be detected using light microscopy. Suitable enzymes include, for example, alkaline phosphatase and horseradish peroxidase. A chromogenic substrate of alkaline phosphatase is PNPP (p-Nitrophenyl Phosphate, Disodium Salt). PNPP produces a yellow water-soluble reaction product that absorbs light at 405 nm. Chromogenic substrates of horseradish peroxidase include ABTS (2,2'-Azinobis [3-ethylbenzothiazoline-6-sulfonic acid]-diammonium salt), which yields a green reaction product, OPD (o-phenylenediamine dihydrochloride) which yields a yellow-orange reaction product, and TMB (3,3',5,5'-tetramethylbenzidine) soluble substrates yield a blue colour when detecting HRP. Other suitable enzyme-substrate combinations, methods of detecting the Ambra-1-ligand and Loricrin-ligand complexes, and suitable detection moieties will be known to those skilled in the art.

In some embodiments, the first and/or second ligand or the capture agent is immobilized on a solid phase surface, for example a microarray, slide, well or bead.

In some embodiments, the expression of Ambra-1 and Loricrin is detected and/or quantified by visual assessment, for example, microscopy. In other embodiments, the expression of Ambra-1 and Loricrin is detected and/or quantified by an automated slide scanner.

According to a ninth aspect of the present invention, there is provided a kit for predicting an increased risk of developing metastasis of a subject suffering from melanoma, the kit comprising:
 a first ligand specific for Ambra-1; and
 a second ligand specific for Loricrin.

In some embodiments, the kit further comprises instructions for using the kit to predict the risk of metastasis in a subject suffering from melanoma.

In some embodiments, the kit further comprises at least one capture agent. Aptly, a capture agent may comprise a detection moiety and a binding moiety specific for the first and/or second ligand.

In some embodiments, the first and/or second ligand and/or the capture agent comprises an enzyme as a detection moiety, and the kit further comprises a substrate of the enzyme.

Aptly, the kit may further comprise one or more additional components such as reagents and/or apparatus necessary for carrying out an in vitro assay, e.g. buffers, fixatives, wash solutions, blocking reagents, diluents, chromogens, enzymes, substrates, test tubes, plates, pipettes etc.

The kit of certain embodiments of the invention may advantageously be used for carrying out a method of certain embodiments of the invention and could be employed in a variety of applications, for example in the diagnostic field or as a research tool. It will be appreciated that the parts of the kit may be packaged individually in vials or in combination in containers or multi-container units. Aptly, manufacture of the kit follows standard procedures which are known to the person skilled in the art.

In some embodiments, a therapeutic agent is administered to the subject no more than 12 weeks, no more than 10 weeks, no more than 6 weeks, no more than 4 weeks, no more than 2 weeks or no more than 1 week after the subject is identified as having a decrease or loss of expression of Ambra-1 and Loricrin in the tissue sample.

In some embodiments, the therapeutic agent is a chemotherapeutic agent. Any available, suitable chemotherapeutic agent may be administered to the subject. As used herein, a "chemotherapeutic agent" means any therapeutic agent useful for the treatment of cancer, and encompasses small molecules as well as biological agents, such as antibodies. In some embodiments, the chemotherapeutic agent is selected from Dacarbazine (DTIC), Temozolomide, Nab-paclitaxel, Paclitaxel, Carmustine (BCNU), Cisplatin, Carboplatin, Vinblastine, interleukin 2, interferon alpha, antibodies (e.g. ipilimumab, anti-PD1 antibody) and B-Raf inhibitors (e.g. vemurafenib, dabrafenib).

Non-limiting routes of administration of the therapeutic agent include by oral, intravenous, intraperitoneal, subcutaneous, intramuscular, topical, intradermal, intranasal or intrabronchial administration (for example as effected by inhalation). In some embodiments, the therapeutic agent is administered parenterally, e.g., intravenously. Common modes of administration by which the therapeutic agent may be administered include, for example, administration as a bolus dose or as an infusion over a set period of time.

A therapeutic agent may be administered in an amount effective to prevent, inhibit or delay the development of metastasis.

Suitable doses and dosage regimes for a given subject and therapeutic agent can be determined using a variety of different methods, such as body-surface area or body-weight, or in accordance with specialist literature and/or individual hospital protocols. Doses may be further adjusted following consideration of a subject's neutrophil count, renal and hepatic function, and history of any previous adverse effects to the therapeutic agent. Doses may also differ depending on whether a therapeutic agent is used alone or in combination.

The skilled person will recognize that further modes of administration, dosages of therapeutic agents and treatment regimens can be determined by the treating physician according to methods known in the art.

Certain embodiments of the present invention provide a method of determining a treatment regime for a subject suffering from melanoma, the method comprising:
 a) obtaining a tissue sample from the subject, wherein the tissue sample comprises tissue overlying a primary melanoma;
 b) determining the expression of Ambra-1 and Loricrin in the tissue sample;
 c) comparing the expression obtained in (b) with a reference tissue or levels obtained therefrom, and d) (i) if expression of Ambra-1 and Loricrin is normal or increased, following a normal recognized care pathway, or
(ii) if expression of Ambra-1 and Loricrin is decreased or lost, treating the subject with a systemic anti-cancer treatment regime.

A "normal recognized care pathway", as will be known to those skilled in the art, will be understood as meaning that a wider excision of the scar left by excision of the primary melanoma is carried out on the subject. The size of the wider excision will be determined by a clinician or surgeon, based on the Breslow depth of the primary melanoma. A normal recognized care pathway may further comprise regular (e.g. every 3-12 months) clinical assessment of the subject for up to 5 years. In some embodiments wherein the primary melanoma is stage 2b or 2c, the normal recognized care pathway may further comprise carrying out a staging CT scan on the subject, from the head to the pelvis, at the time of diagnosis. Some treatment centres offer staging sentinel lymph node biopsy of all stage 2a, 2b and 2c tumours. Thus, in some embodiments, the normal recognized care pathway may further comprise carrying out a sentinel lymph node biopsy.

In some embodiments, a systemic anti-cancer treatment regime comprises administering a therapeutic agent to the subject.

Certain embodiments of the present invention provide a method for the treatment of a subject suffering from melanoma.

Ideally, a subject identified as having an increased risk of metastasis is treated as soon as possible to minimize the chances of development of metastasis. Thus, in some embodiments the method or treatment regime is for preventing, inhibiting or delaying metastasis or decreasing the risk of metastasis in the subject.

In some embodiments, a subject is treated immediately or shortly after being identified as having an increased risk of metastasis.

In some embodiments, treatment with the therapeutic agent is carried out after surgery to excise the primary melanoma.

In some embodiments, a method of treatment or a treatment regime may further include one or more of: intensified imaging (e.g. CT scan, PET, MRI, X-ray) of the subject; discussion and/or offering of, or carrying out, a sentinel lymph node biopsy; partial or complete lymphadenectomy; inclusion of the subject in clinical trials; and radiation therapy.

DETAILED DESCRIPTION OF CERTAIN EMBODIMENTS

Embodiments of the invention will now be described by way of example only, and with reference to the accompanying Figures in which:

FIGS. 1A-1D are light microscopy images showing Ambra-1 expression in normal epidermis (FIG. 1A) and peri-tumoural epidermis (FIGS. 1B-1D) overlying AJCC stage I melanomas. Scale bars: 50 µm.

Figure 3A:
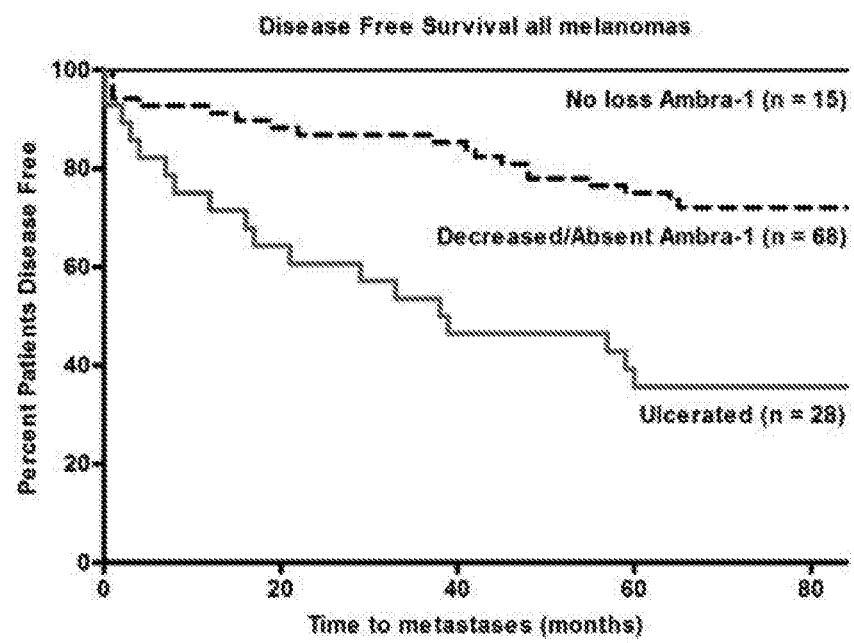
Figure 3B:
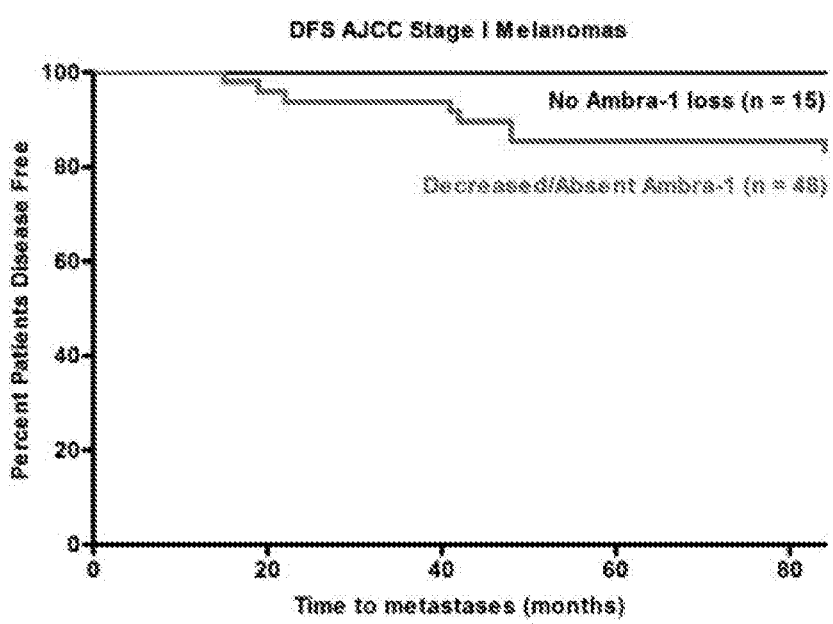
Figure 4A:
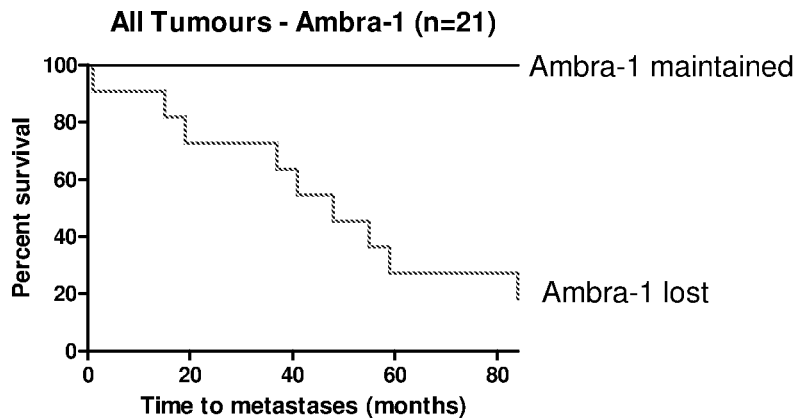
Figure 4B:
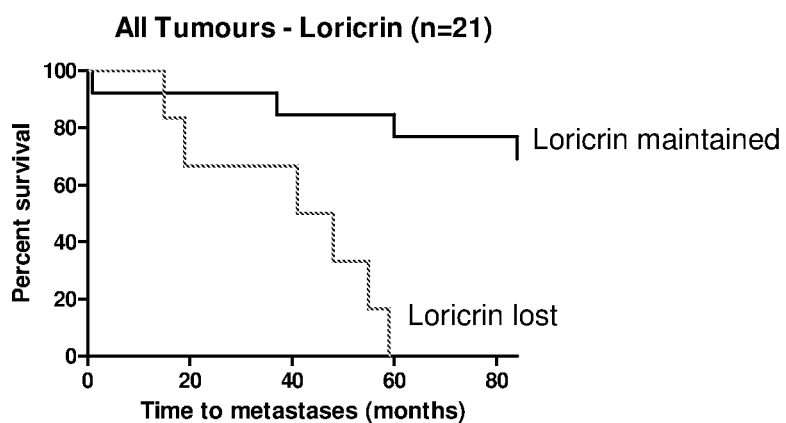
Figure 4C:
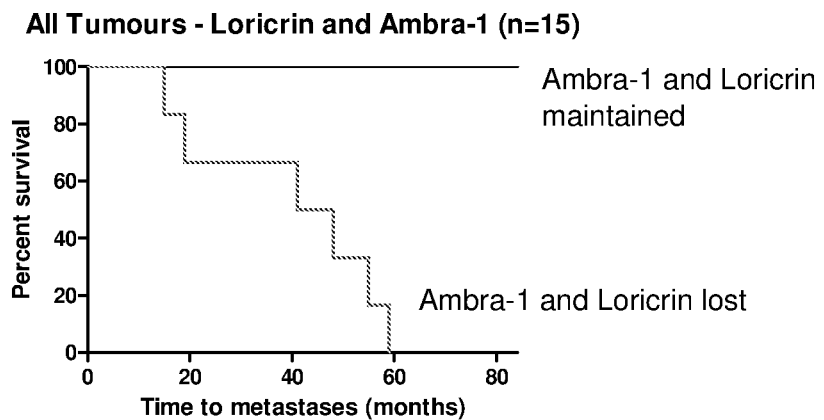
Figure 5A:
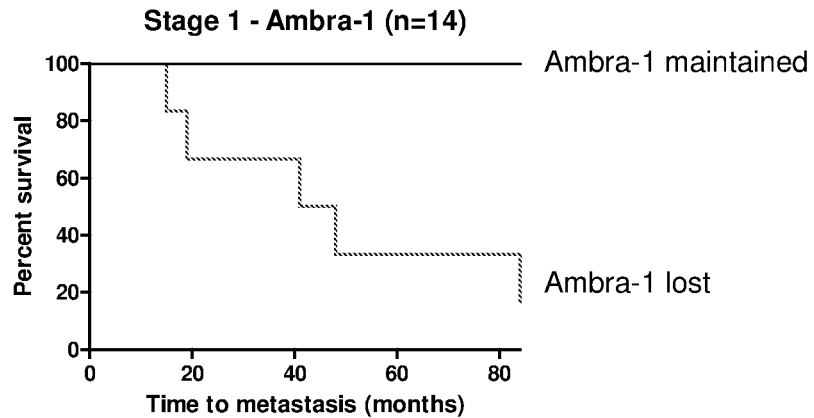
Figure 5B:
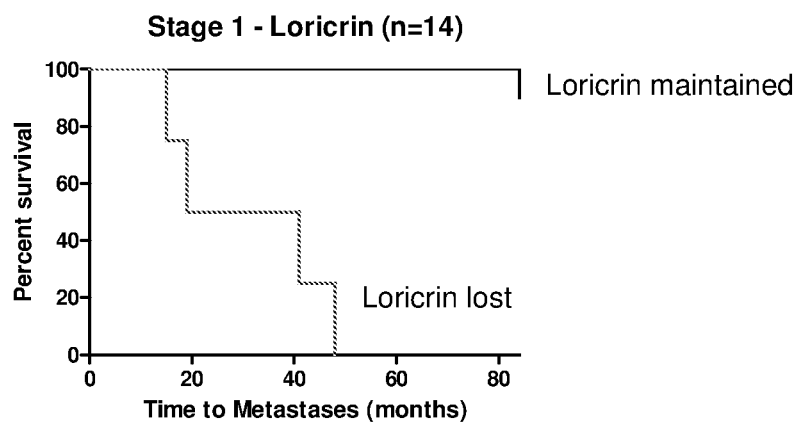
Figure 5C:
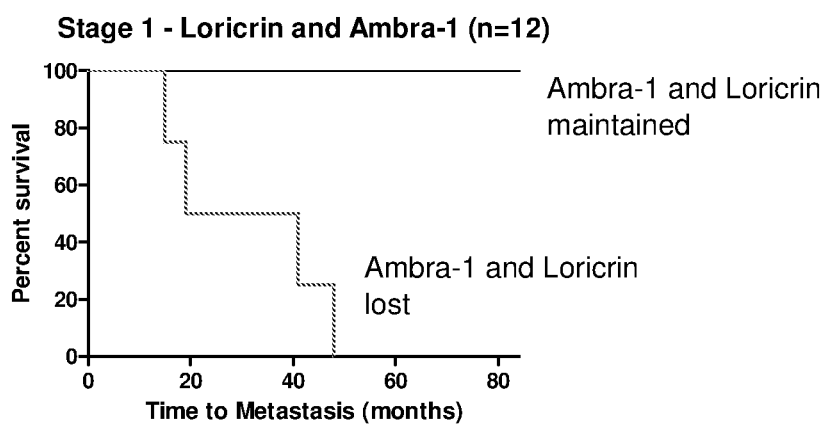

FIG. 3A shows univariate analysis of epidermal Ambra-1 expression in all AJCC stage melanomas. Kaplan-Meier curve showing 7-year Disease Free Survival (months until first metastasis detected) in primary melanoma epidermises with no alteration in Ambra-1 expression (top line), decreased or absent Ambra-1 expression (dashed line) or ulcerated tumours (bottom line). Log-Rand (Mantel-Cox) Test P<0.0001. DFS=100% no Ambra-1 loss, 72.1% decreased or absent Ambra-1, 35.7% ulcerated. Direct analysis of No loss Ambra-1 and decreased/absent Ambra-1 Log-Rank (Mantel-Cox) Test P=0.0270, HR 3.56 (95% Cl 1.16-10.93);

FIG. 3B shows multivariate analysis of Ambra-1 expression in pilot cohort of AJCC stage 1 melanomas. Kaplan-Meier curve showing 7-year Disease Free Survival (months until first metastasis detected) in AJCC stage 1 primary melanoma epidermises that revealed no alteration in Ambra-1 expression (top line) compared to stage 1 tumours with absent epidermal Ambra-1 (bottom line). DFS=100% no Ambra-1 loss, 83.3% decreased or absent Ambra-1. Log-Rank (Mantel-Cox) Test P=0.0575, HR 4.29 (95% Cl 0.95-19.25);

FIG. 4A is a Kaplan-Meier curve showing 7-year Disease Free Survival (months until first metastasis detected) in epidermises in which Ambra-1 expression was maintained (top line) compared to those in which expression of Ambra-1 was lost (bottom line), across all tumour types. P=0.0007, HR 10.1 (95% Cl 2.65-38.5);

FIG. 4B is a Kaplan-Meier curve showing 7-year Disease Free Survival (months until first metastasis detected) in epidermises in which Loricrin expression was maintained (top line) compared to those in which expression of Loricrin was lost (bottom line), across all tumour types. P=0.0006, HR 18.4 (95% Cl 3.5-96.2);

FIG. 4C is a Kaplan-Meier curve showing 7-year Disease Free Survival (months until first metastasis detected) in epidermises in which both Ambra-1 and Loricrin expression was maintained (top line) compared to those in which expression of Ambra-1 and Loricrin was lost (bottom line), across all tumour types. P=<0.0001, HR 39.6 (95% Cl 6.4-243.9);

FIG. 5A is a Kaplan-Meier curve showing 7-year Disease Free Survival (months until first metastasis detected) in AJCC stage 1 primary melanoma epidermises in which Ambra-1 expression was maintained (top line) compared to those in which Ambra-1 expression was lost (bottom line). P=0.001, HR 24.12 (95% Cl 3.6-161);

FIG. 5B is a Kaplan-Meier curve showing 7-year Disease Free Survival (months until first metastasis detected) in AJCC stage 1 primary melanoma epidermises in which Loricrin expression was maintained (top line) compared to those in which Loricrin expression was lost (bottom line). P<0.0001, HR 210 (95% Cl 16.86-2624);

FIG. 5C is a Kaplan-Meier curve showing 7-year Disease Free Survival (months until first metastasis detected) in AJCC stage 1 primary melanoma epidermises in which both Ambra-1 and Loricrin expression was maintained (top line) compared to those in which Ambra-1 and Loricrin expression was lost (bottom line). P=0.0002, HR 93.5 (95% Cl 8.67-1008);

FIG. 6 shows the amino acid sequence of Homo sapiens Ambra-1 from UniProtKB (primary accession number Q9C0C7-1, isoform 1) (SEQ ID NO. 1); and FIG. 7 shows the amino acid sequence of Homo sapiens Loricrin from UniProtKB (primary accession number P23490) (SEQ ID NO. 2).

FIG. 8 shows a range of microscopy images of Ambra-1 (anti-Ambra-1 antibody (Abcam Biochemicals, Cambridge, UK; 69501; 1:200)) expression in normal epidermis (a), or overlying stage 1 melanomas (b). Ambra-1 maintained, (c). Ambra-1 decreased and (d) Ambra-1 completely lost).

Figure 9:
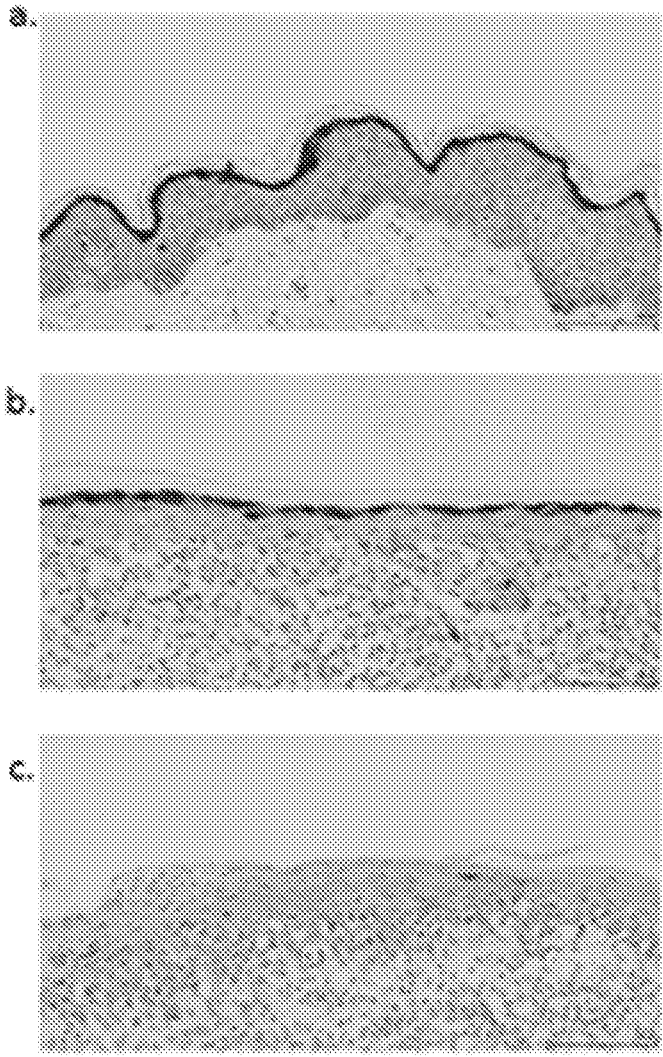

FIG. 9 shows a range of microscopy images of loricrin (anti-Loricrin antibody (Abcam Biochemicals, Cambridge, UK; 24722; 1:500)) expression in normal epidermis (a), or overlying stage 1 melanomas (b) Loricrin maintained, (c) Loricrin completely lost.

Figure 10:
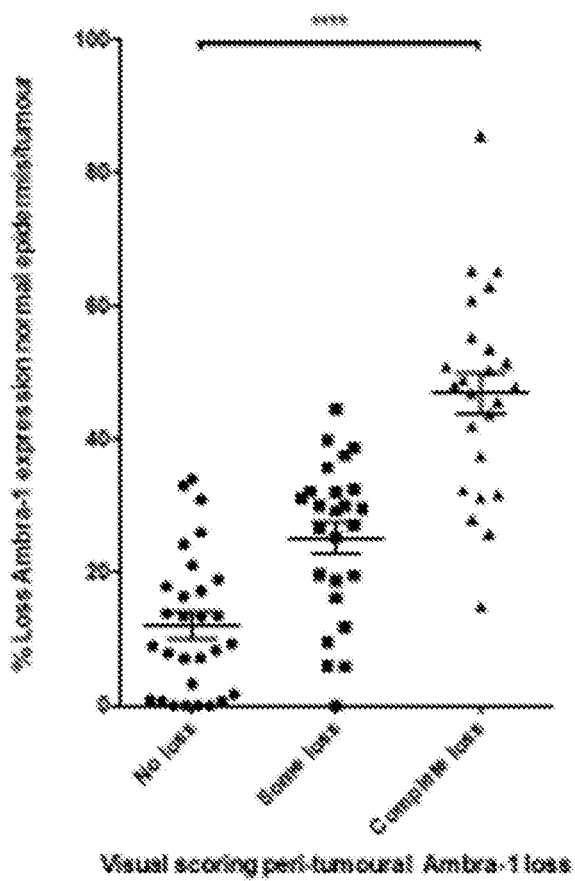

FIG. 10 shows the association between the visual scoring given to the change of peri-tumoural Ambra-1 (no loss, some loss or complete loss) compared to the quantitative analysis results of the percentage decrease in staining positivity in normal epidermis compared to the peri-tumoural epidermis. Horizontal lines represent the mean scoring percentage ± standard error of the mean (0=12.05, 1=25.16, 3=46.92). One way ANOVA P<0.0001****

Figure 11:
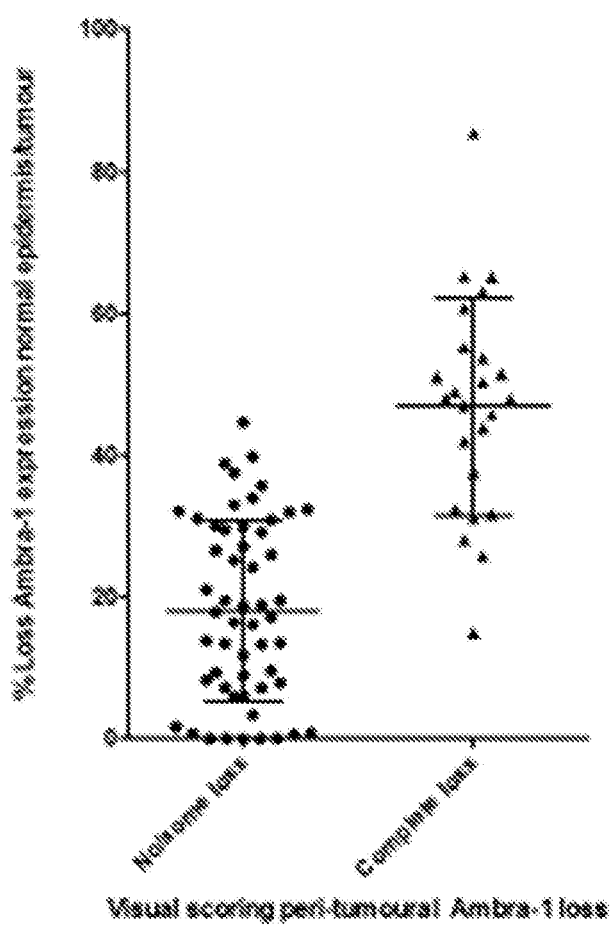

FIG. 11 shows the association between the visual scoring given to the change of peri-tumoural Ambra-1 with no or some loss of staining compared to complete loss of staining. Horizontal lines represent the mean scoring percentage±standard deviation (No/some loss mean=18.12 SD 12.97, complete loss mean=46.92 SD 15.34). Mann-Whitney P<0.0001****

Figure 12:
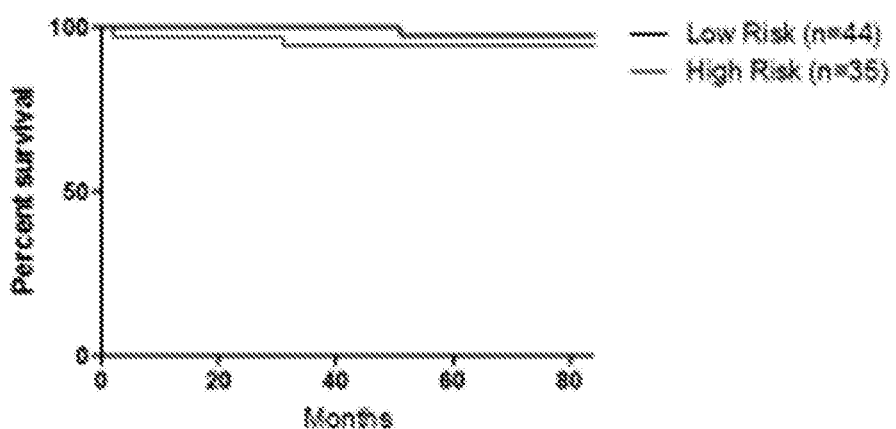

FIG. 12 shows univariate analysis of epidermal Ambra-1 expression in all AJCC stage 1 melanomas. Kaplan-Meier curve showing 7-year Disease Free Survival (months until first metastasis detected) in primary melanoma epidermises with no loss or reduced Ambra-1 expression (black line), versus absent Ambra-1 expression (red line). DFS=97.7% no loss/decreased Ambra-1 (n=44), 94.3% absent Ambra-1 (n=35). Log-Rank (Mantel-Cox) Test P=0.411, HR 2.59 (95% Cl 0.26-25.05).

Figure 13:
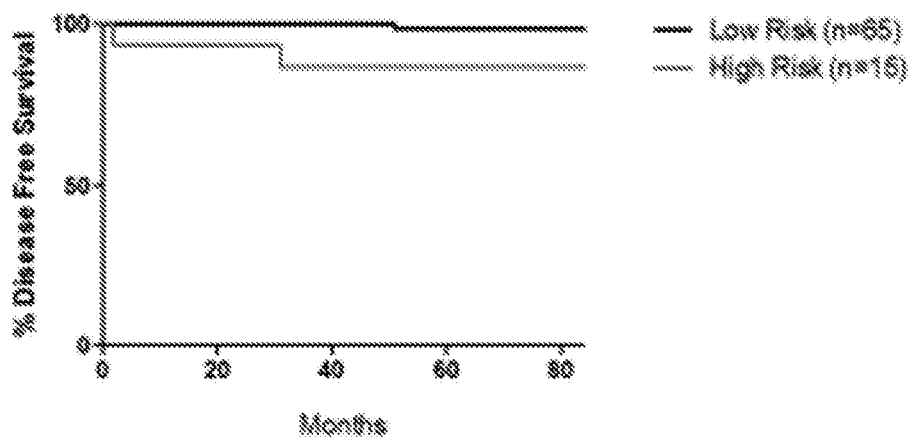

FIG. 13 shows univariate analysis of epidermal Ambra-1 and Loricrin combined expression in all AJCC stage 1 melanomas. Kaplan-Meier curve showing 7-year Disease Free Survival (months until first metastasis detected) in primary melanoma epidermises maintenance of some epidermal Ambra-1 or Loricrin expression ("Low risk" black line), versus loss of both Ambra-1 and loricrin epidermal expression ("High risk" red line). DFS=98.46% Low risk (n=65), 86.67% High risk (n=15). Log-Rank (Mantel-Cox) Test P=0.025, HR 9.29 (95% Cl 1.49-558.0).

Further details of certain embodiments of the invention are provided below.

Definitions

The term "antibody" as used herein is intended to include monoclonal antibodies, polyclonal antibodies, chimeric antibodies, humanised antibodies, bi-specific antibodies, antibody-drug conjugates, and domains and fragments of antibodies including Fab, Fab', F(ab')2, scFv, dsFv, ds-scFv, dimers, minibodies, diabodies, and multimers thereof. Antibodies can be fragmented using conventional techniques. Antibodies may be from any animal origin, including birds and mammals (e.g., human, murine, donkey, sheep, rabbit, goat, guinea pig, camel, horse, or chicken), transgenic animals, or from recombinant sources. Antibodies may be prepared using methods known to those skilled in the art.

As used herein, the term "primary melanoma" refers to a malignant tumour on the skin at the site of origin, regardless of thickness, in patients without clinical or histologic evidence of regional or distant metastatic disease.

As used herein, the wording "tissue overlying a primary melanoma", refers to epidermal tissue situated between a primary melanoma and the surface of the skin.

As used herein, the term "normal tissue" includes for example "normal epidermis", which is healthy (i.e. disease-free) epidermis. In some embodiments, the normal tissue is epidermis that lies adjacent to the primary melanoma, for example within a cuff of normal skin taken with the primary melanoma sample.

As used herein, "peri-tumoural epidermis" refers to epidermal tissue overlying or situated around a tumour.

As used here in, "metastasis" is defined as the recurrence or disease progression that may occur locally (such as local recurrence and in transit disease), regionally (such as nodal micrometastasis or macrometastasis), or distally (such as brain, lung and other tissues). In some embodiments, the term "metastasis" is used to refer to metastatic disease following a primary melanoma. Typically, metastasis originating from a primary melanoma may spread to the lungs and/or brain of the subject as well as other locations.

It is to be understood that the term "comparing" and "compare" as used herein usually refers to a comparison of corresponding parameters or levels, e.g., an absolute amount is compared to an absolute reference amount while a concentration is compared to a reference concentration or a signal intensity signal obtained from the tissue sample is compared to the same type of signal intensity obtained from the reference. The comparison may be carried out manually, for example by visual assessment, or it may be automated (e.g. using an automated scanner or computer-assisted). Thus, the comparison may be carried out by a computing device.

The stage of a melanoma is a description of how widespread it is. This includes its thickness in the skin, whether it has spread to nearby lymph nodes or any other organs, and certain other factors. The stage is based on the results of the physical exam, biopsies, and any imaging tests (CT or MRI scan, etc.) or other tests that have been done. Such tests will be known to those skilled in the art. The system most often used to stage melanoma is the American Joint Commission on Cancer (AJCC) TNM system. Table 1 describes the features identifying each stage.

TABLE 1

| | Stage 1 |
| --- | --- |
| 1a Tumour | <1.00 mm without ulceration; no lymph node involvement, no distant metastases. |
| 1b Tumour | <1.00 mm with ulceration or Clark level IV or V tumour 1.01-2.0 mm without ulceration; no lymph node involvement; no distant metastases. |
| | Stage 2 |
| 2a Tumour | 1.01-2.0 mm with ulceration; tumour 2.01-4.0 mm without ulceration; no lymph node involvement; no distant metastases. |
| 2b Tumour | 2.01-4 mm with ulceration. |
| 2b Tumour | >4.0 mm without ulceration; no lymph node involvement; no distant metastases. |
| 2c Tumour | >4.0 mm with ulceration; no nodal involvement; no distant metastases. |
| | Stage 3 |
| 3a | Tumour of any thickness without ulceration with 1 positive lymph node and micrometastasis or macrometastasis. |
| 3b | Tumour of any thickness without ulceration with 2-3 positive lymph nodes and micrometastasis or macrometastasis. |
| 3c | Tumour of any thickness and macrometastasis OR in-transit met(s)/satellite(s) without metastatic lymph nodes, OR 4 or more metastatic lymph nodes, matted nodes or combinations of in-transit met(s)/satellite(s), OR ulcerated melanoma and metastatic lymph node(s). |
| | Stage 4 |
| 4 | Tumour of any thickness with any nodes and any metastases |

EXAMPLES

Materials and Methods

Example 1

Immunohistochemistry for Ambra-1 and Loricrin

Analysis of primary melanoma tissue from the patient cohort shown in Table 2 was performed by immunohistochemical staining of formalin-fixed paraffin-embedded sections. Tissue sections of 5-6 µm thickness were baked onto X-TRA® microscope slides (Leica Microsystems, Milton Keynes, UK) at 56° C. overnight. They were then incubated in HISTOCLEAR® (AGTC Bioproducts, Hessle, UK) for 20 minutes before rehydration in 100%, 75%, 50% ethanol and then distilled water for 5 seconds each. Antigen retrieval was undertaken by microwave heating in preheated antigen retrieval buffers (Ambra-1 (10 mM Tris-HCl (pH 7.6)), Loricrin (10 mM Na-Citrate (pH 6.0)) for 12 minutes before being allowed to cool for 20 minutes. Each section was allowed to dry and the tissue isolated with an IMMEDGE™ hydrophobic pen (Vector Laboratories Inc., Burlingame, USA). Sections were then incubated with PBS/0.05% TWEEN® (PBS/T) for 3 minutes to allow rehydration before incubation with 0.2% TRITON™ X-100 (Sigma, St. Louis, USA) in PBS/T for 10 minutes. After washing with PBS/T sections were incubated in 3% $H_2O$ in water for 10 minutes to block endogenous peroxidase. Endogenous Avidin was blocked with the Avidin solution of an Avidin/Biotin Blocking kit (Vector Laboratories Inc., Burlingame, USA) for 15 minutes, before further washing with PBS/T and incubation with the Biotin portion of the kit for 15 minutes, with a following PBS/T wash. Protein blocking was undertaken by incubating sections in 2% blocking serum from an animal specific VECTASTAIN® Elite kit (Vector Laboratories Inc., Burlingame, USA).

Following a further PBS/T wash, sections were incubated with primary antibody for 1 hour at room temperature with anti-Ambra-1 antibody (Abcam Biochemicals, Cambridge, UK; 69501; 1:200) or anti-Loricrin antibody (Abcam Biochemicals, Cambridge, UK; 24722; 1:500). After 3 washes with PBS/T primary antibody was detected with biotinylated animal specific secondary antibody for 30 minutes at room temperature before 3 further washes with PBS/T. Staining was performed through incubation for 30 minutes with the ABC reagents from the VECTASTAIN® Elite kit (premixed 30 minutes prior to use), followed by 3 washes with PBS/T and then a 10 minute incubation with VIP solution (Vector Laboratories Inc., Burlingame, USA). Slides were rinsed in tap water for 5 minutes before counter staining with haematoxylin (Sigma Diagnostics, St. Louis, USA) for 2 minutes followed by a final 10 minute wash in tap water with frequent changes. After dehydration through 75% and 100% ethanol for 5 seconds sections were cleaned for 2 minutes in HISTOCLEAR®, allowed to dry, then coverslips mounted with DPX mountant (VWR International Ltd., Poole, UK).

Determination of Expression

The difference in expression levels of Ambra-1 and/or Loricrin between the normal epidermis and peri-tumoural epidermis was initially determined by consensus agreement of 3 Dermatologists and a Histopathologist. Expression was quantified by assessing the percentage of positively stained cells in the peri-tumoural as a percentage of the Ambra-1/Loricrin expression determined in the internal control reference of the adjacent normal epidermis using Leica QWin image analysis software (Leica Microsystems). These observations were categorized as either "maintained" (>75% of normal expression), "decreased" (25-75% of normal expression) or "lost" (<25% of normal expression). Assessment of each section was undertaken without prior knowledge of eventual disease outcome.

TABLE 2

| Patient Cohort | |
|---|---|
| Number of Patients | 129 |
| Male:Female | 66:62 |
| Median age at diagnosis (range) | 58 (17-87) |
| AJCC stage at diagnosis | |
| 1a | 40 |
| 1b | 36 |
| 2a | 22 |
| 2b | 18 |
| 2c | 12 |
| Eventual AJCC stage (8 years follow-up) | |
| 1a | 38 |
| 1b | 27 |
| 2a | 12 |
| 2b | 7 |
| 2c | 4 |
| 3 | 15 |
| 4 | 25 |
| Median Breslow depth (range) | 1.55 mm (0.3-15) |
| Ulcerated primary tumours | 28 |

Statistics

All statistical analysis and image generation was undertaken using GraphPad Prism 5 (GraphPad Software; San Diego, USA) statistical analysis software.

All univariate and multivariate analysis of study variables for Disease Free Survival were undertaken using Kaplan-Meier curve constructions against 8-year follow-up, as well as log-rank (Mantel-Cox) analysis of the comparative data.

Example 1

Results and Discussion

The present inventors identified that a decrease of Ambra-1 expression in the peri-tumoural epidermis overlying melanomas, in particular in AJCC stage I melanomas, significantly correlates with decreased Disease Free Survival over 7 years. As shown in FIG. 1A, Ambra-1 expression is increased from the basal layer towards the stratum corneum in the normal epidermis situated adjacent to an AJCC stage 1 melanoma consistent with maintained differentiation. However, Ambra-1 expression is maintained (FIG. 1B), decreased (FIG. 1C) or even lost (FIG. 1D) in the epidermis overlying a range of AJCC stage 1 tumours.

Referring to FIG. 3, the loss or decrease of epidermal Ambra-1 expression correlates with an increased risk of metastasis. Across all AJCC melanomas (FIG. 3A), 100% of patients displaying no loss of Ambra-1 expression were disease free after 7 years. This decreased to 72.1% in patients with decreased or absent expression of Ambra-1. Only 35.7% of patients with ulcerated melanomas were disease free after 7 years. This highlights a stepwise increase in disease risk with loss of Ambra-1 and eventual associated frank ulceration of the tumour.

Taking AJCC stage 1 melanomas only (FIG. 3B), the percentage of patients who were disease free after 7 years was 100% for those with no loss of Ambra-1 expression, reduced to 83.3% for those with decreased or absent Ambra-1 expression.

FIGS. 4A and 5A show the correlation between expression of Ambra-1 and disease free survival of subjects in a smaller cohort in which both Ambra-1 and Loricrin expression were assessed, over 7 years for all tumour types (FIG. 4A) or stage 1 only (FIG. 5A). Across all tumour types (FIG. 4A), all patients in which expression of Ambra-1 was maintained were disease free after 7 years. For those in which Ambra-1 expression was lost, only 18% were disease free after 7 years. For stage 1 tumours, again 100% of patients with maintained expression of Ambra-1 did not develop metastasis, while the disease-free survival rate was 17% for those with loss of Ambra-1 expression.

Contrary to the current publications in the art which implicate Ambra-1 in the control of autophagy, Ambra-1's role in this context is thought to be in the down-regulation of differentiation with the normal epidermis resulting in a loss of integrity. It has been demonstrated by the inventors that the down-regulation of other autophagy proteins, such as ATG1, do not affect the differentiation process, supporting the hypothesis that this process is not related to autophagy.

Figure 2:
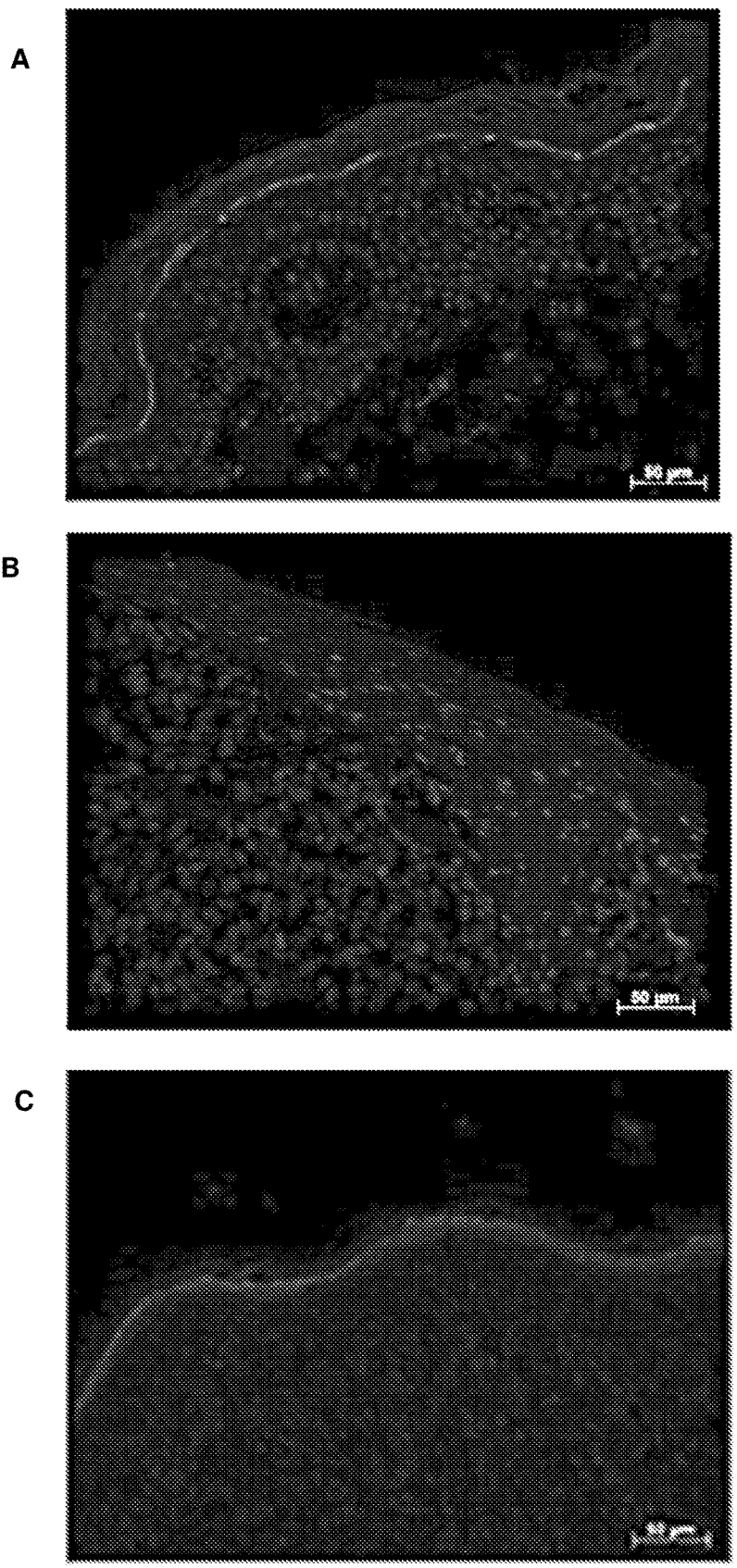
FIGS. 2A-2C are immunofluorescent microscopy images showing Loricrin expression in normal epidermis (FIG. 2A), and peri-tumoural epidermis (FIGS. 2B-2C) overlying AJCC stage I melanomas. Scale bars: 50 µm).

Unexpectedly, it was found that a loss of Loricrin expression also correlates with an increased risk of metastasis. FIGS. 2A-C show representative images of normal Loricrin expression in the stratum corneum (FIG. 2A) as well as in peri-tumoural epidermis in which Loricrin expression is lost (FIG. 2B or maintained (FIG. 2C).

Referring to FIGS. 4B and 5B, the loss or decrease of epidermal Loricrin expression correlates with decreased disease-free survival over 7 years. Across all AJCC melanomas (FIG. 4B), 64% of patients for whom Loricrin expression was maintained were disease free after 7 years. However, no patients with loss of Loricrin expression were disease-free after 5 years. For AJCC stage 1 melanomas (FIG. 5B), 100% of patients in which Loricrin expression was maintained were disease free after 7 years. No patients with loss of Loricrin expression were disease-free after 5 years. This demonstrates a statistical significant correlation between Loricrin expression and disease-free survival rates in melanoma patients. However, as with Ambra-1, the loss of Loricrin alone is not predictive of disease progression with 100% accuracy, either for AJCC stage 1 melanoma or all tumour stages (see Table 3).

However, the inventors have determined that determination of expression of both Ambra-1 and Loricrin is strongly representative of disease progression to metastasis. The results of these experiments are shown in FIGS. 4C and 5C, and summarized in Table 3.

TABLE 3

| Marker | Sensitivity | Specificity | PPV[1] | NPV[2] |
| --- | --- | --- | --- | --- |
| All tumour stages n = 15 | | | | |
| Loss of Ambra-1 | 100% | 80% | 83.3% | 100% |
| Loss of Loricrin | 63.6% | 100% | 100% | 69.2% |
| Loss of Ambra-1 + Loricrin | 100% | 100% | 100% | 100% |
| Stage 1 melanoma n = 12 | | | | |
| Loss of Ambra-1 | 100% | 88.9% | 83.3% | 100% |
| Loss of Loricrin | 80% | 100% | 100% | 90% |
| Loss of Ambra-1 + Loricrin | 100% | 100% | 100% | 100% |

[1]Positive predictive value
[2]Negative predictive value

Thus, it was found that the combination of loss of Ambra-1 and loss of Loricrin identifies with 100% accuracy patients which went on to develop metastasis.

Example 2

Further analysis was carried out on 80 retrospective AJCC stage 1 melanoma patients' samples recruited to an independent James Cook University Hospital melanoma cohort (Table 4). The analysis reveals data in keeping with the findings in the initial retrospective cohort detailed above.

TABLE 4

| Number of Patients | 80 |
| --- | --- |
| Male:Female | 27:53 |
| AJCC stage at diagnosis | |
| 1a | 54 |
| 1b | 26 |
| Eventual AJCC stage (7 years follow-up) | |
| 1a | 53 |
| 1b | 24 |
| 4 | 3 |
| Mean Breslow depth (range) | 0.83 mm (0.14-1.9) |

Immunohistochemical staining was undertaken using DAB counterstain as the most widely used specialist stain in clinical use. All samples were digitally imaged using automated scanning of slides on a Leica SCN400 digital slide scanner (Leica Biosystems) within the Newcastle University Biobank (FIGS. 8 and 9).

Visual analysis of epidermal Ambra-1 loss was undertaken by two independent dermatologists and scores assigned for each slide based on the degree of loss of epidermal Ambra-1 in the peri-tumoural epidermis compared to normal epidermis within the same section. There was 95% concordance in scores given between dermatologists, and further review of these slides resulted in an agreed score for each.

Similarly, the same two dermatologists undertook visual analysis of epidermal Loricrin loss independently. Any break in the continuity of the loricrin stain in the peri-tumoural epidermis that was not due to direct tumour invasion of the upper epidermis was scored as Loricrin loss. Concordance was 97.5% with agreement reached for all samples.

Quantitative analysis of epidermal Ambra-1 was undertaken using the Leica Slidepath systems' previously validated analysis software. Five representative areas of normal epidermis were selected at 200× magnification and the mean percentage of DAB positive pixels obtained. This was compared to the mean percentage of DAB positive pixels in ten representative areas of peri-tumoural epidermis at ×200 magnification. The overall percentage decrease in Ambra-1 expression between peri-tumoural expression and that of the normal epidermis was then calculated.

Comparison of visual and quantitative scores (FIG. 10) reveals a statistically significant (P<0.0001) stepwise increase in quantitative score with decreased peri-tumoural Ambra-1 as analyzed visually. This validates visual scoring as a robust and reliable method for analyzing Ambra-1 epidermal staining.

To determine a cut-point for survival analysis, visual and quantitative scores were re-analyzed with no or some loss of peri-tumoural Ambra-1 compared to complete loss (FIG. 11). This shows a statistically significant increase in qualitative score in samples scored visually as having a complete loss of Ambra-1 (P<0.0001). This further validates the appropriateness of visual scoring to identify samples with complete loss of peri-tumoural Ambra-1, and one standard deviation below the mean for complete Ambra-1 loss (46.92 mean SD 15.34) gives an appropriate cut off of 30% to determine further qualitative analysis of Ambra-1 loss.

Univariate analysis of peri-tumoural Ambra-1 loss in all patients revealed no overall difference in disease free survival between "High risk" (tumours with complete peritumoural Ambra-1 loss as determined by a qualitative decrease in expression of >30%) and "Low risk" tumours (qualitative expression decrease <30%) (FIG. 5). DFS=97.7% Low risk tumours (n=44), 94.3% High risk tumours (n=35). Log-Rank (Mantel-Cox) Test P=0.411, HR 2.59 (95% Cl 0.26-25.05). These results do not support Ambra-1 as a prognostic biomarker in this subset of patients.

To assess the validity of the combination of epidermal Ambra-1 and Loricrin expression as a prognostic biomarker, univariate analysis was undertaken in all samples. "High risk" samples were determined as having complete peritumoural Ambra-1 loss (>30% decrease quantitatively) AND a loss of loricrin. All other tumours, with either loss of Ambra-1 OR Loricrin, were deemed "Low risk". These results showed a statistically significant increased risk of metastases in the High risk tumour group, even though the total number of metastatic events was low; further reinforcing the utility of the combination of Ambra-1 and Loricrin as a combined prognostic biomarker in AJCC stage 1 disease. DFS=98.46% Low risk (n=65), 86.67% High risk (n=15). Log-Rank (Mantel-Cox) Test P=0.025, HR 9.29 (95% Cl 1.49-558.0).

TABLE 5

| Marker (n = 80) | Sensitivity | Specificity | PPV | NPV |
|---|---|---|---|---|
| Loss of Ambra | 67% | 57% | 6% | 97.7% |
| Loss of Loricrin | 67% | 70% | 8% | 98.1% |
| Combined loss of Ambra and Loricrin | 67% | 83% | 13% | 98.4% |

The final analysis of the combined Ambra-1/Loricrin biomarker highlights increased specificity (83%), positive and negative predictive values (13% and 98.4% respectively) of Ambra-1/Loricrin combined over and above either Ambra-1 or loricrin alone (Table 5). This indicates that the combined biomarker would add prognostic value in identifying high-risk patients for increased surveillance, as well as identifying low-risk patients that could be reassured regarding their prognosis with more certainty.

This is an important finding as a decrease or loss of expression of these two proteins may indicate a breakdown of the epidermis overlying and the vasculature underlying the tumour, meaning that cancer cells may have already migrated from the primary tumour at the time of tumour excision.

Certain embodiments of the present invention thus provides a means for determining whether a subject suffering from melanoma is at increased risk of metastasis. This allows a treatment regime to be tailored accordingly, thereby reducing the risk of the subject developing metastasis and improving their prognosis.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An in vitro method comprising:

contacting tissue overlying a primary melanoma obtained from a subject suffering from melanoma with a first ligand specific for Ambra-1 comprising the sequence shown in SEQ ID NO. 1, the first ligand comprising an anti-Ambra-1 antibody, wherein the presence of Ambra-1 creates an Ambra-1-ligand complex;

contacting the tissue overlying a primary melanoma with a second ligand specific for Loricrin comprising the sequence shown in SEQ ID NO. 2, the second ligand comprising an anti-Loricrin antibody, wherein the presence of Loricrin creates a Loricrin-ligand complex; and detecting a co-occurrence of a decrease in the expression of Ambra-1 having the sequence shown in SEQ ID NO. 1 and a decrease in the expression of Loricrin having the sequence shown in SEQ ID NO. 2 in the tissue sample compared to a control reference of adjacent normal epidermis, or a loss of expression of Ambra-1 and a loss of expression of Loricrin in the tissue sample by detecting and/or quantifying the Ambra-1-ligand complex and the Loricrin-ligand complex; and predicting an increased risk of metastatic disease following a primary melanoma in the subject if there is a co-occurrence of a decrease in the expression of Ambra-1 and a decrease in the expression of Loricrin in the tissue sample compared to the control reference of adjacent normal epidermis.

2. The method according to claim 1, wherein the Ambra-1-ligand complex and the Loricrin-ligand complex are detected and/or quantified by visual assessment or by an automated slide scanner.

3. The method according to claim 1, wherein the tissue sample comprises tissue overlying a primary melanoma and a portion of normal epidermis adjacent to the primary melanoma.

4. The method according to claim 1, wherein the expression of Ambra-1 and Loricrin in the tissue sample is from 25% to 75% of the respective reference level.

* * * * *